US012414983B2

(12) United States Patent
Olin

(10) Patent No.: US 12,414,983 B2
(45) Date of Patent: Sep. 16, 2025

(54) CD200AR LIGANDS FOR CANCER IMMUNOTHERAPY

(71) Applicant: REGENTS OF THE UNIVERSITY OF MINNESOTA, Minneapolis, MN (US)

(72) Inventor: Michael Olin, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 1031 days.

(21) Appl. No.: 17/422,641

(22) PCT Filed: Jan. 13, 2020

(86) PCT No.: PCT/US2020/013349
§ 371 (c)(1),
(2) Date: Jul. 13, 2021

(87) PCT Pub. No.: WO2020/150149
PCT Pub. Date: Jul. 23, 2020

(65) Prior Publication Data
US 2022/0088134 A1 Mar. 24, 2022

Related U.S. Application Data

(60) Provisional application No. 62/792,311, filed on Jan. 14, 2019.

(51) Int. Cl.
*A61K 38/17* (2006.01)
*A61K 39/00* (2006.01)
*A61K 39/39* (2006.01)
*A61P 35/00* (2006.01)

(52) U.S. Cl.
CPC ...... *A61K 38/1774* (2013.01); *A61K 39/0011* (2013.01); *A61K 39/39* (2013.01); *A61P 35/00* (2018.01); *A61K 2039/5152* (2013.01); *A61K 2039/545* (2013.01)

(58) Field of Classification Search
CPC ...... A61K 2039/5152; A61K 2039/545; A61K 2039/572; A61K 38/10; A61K 39/39; A61K 38/1703; A61K 39/0011; A61K 2039/552; A61K 45/06; A61K 2300/00; A61P 35/00
See application file for complete search history.

(56) References Cited

U.S. PATENT DOCUMENTS

| 4,559,157 A | 12/1985 | Smith et al. |
|---|---|---|
| 4,608,392 A | 8/1986 | Jacquet et al. |
| 4,683,202 A | 7/1987 | Mullis |
| 4,820,508 A | 4/1989 | Wortzman |
| 4,873,192 A | 10/1989 | Kunkel |
| 4,938,949 A | 7/1990 | Borch et al. |
| 4,992,478 A | 2/1991 | Geria |
| 5,350,674 A | 9/1994 | Boenisch et al. |
| 5,585,362 A | 12/1996 | Schwarz et al. |
| 5,744,585 A | 4/1998 | Medenica et al. |
| 5,928,906 A | 7/1999 | Koster et al. |
| 6,955,811 B2 | 10/2005 | Gorczynski et al. |
| 7,205,386 B2 | 4/2007 | Gorczynski |
| 7,902,151 B2 | 3/2011 | Gorczynski et al. |
| 8,709,415 B2 | 4/2014 | Bowdish et al. |
| 9,737,598 B2 | 8/2017 | Olin et al. |
| 10,183,060 B2 * | 1/2019 | Schreiber ............... A61P 37/04 |
| 10,576,145 B2 | 3/2020 | Olin |
| 10,888,609 B2 * | 1/2021 | Olin ........................ C07K 7/08 |
| 11,666,645 B2 * | 6/2023 | Olin ........................ C07K 7/06 424/185.1 |
| 11,826,408 B2 * | 11/2023 | Olin ..................... A61K 9/0019 |
| 2002/0168364 A1 | 11/2002 | Gorczynski et al. |
| 2010/0291085 A1 | 11/2010 | Rother et al. |
| 2013/0331546 A1 | 12/2013 | Ohlfest et al. |
| 2016/0166680 A1 | 6/2016 | Olin |
| 2018/0326028 A1 | 11/2018 | Plin |
| 2021/0106665 A1 | 4/2021 | Olin |

FOREIGN PATENT DOCUMENTS

| WO | 2012048190 A1 | 4/2012 | |
|---|---|---|---|
| WO | 2013076374 A1 | 5/2013 | |
| WO | WO-2017079335 A1 * | 5/2017 | ......... A61K 39/0011 |

OTHER PUBLICATIONS

Ali, S., et al., "Combined immunostimulation and conditional cytotoxic gene therapy provide long-term survival in a large glioma model", Cancer Res 65(16), 7194-7204 (2005).
Anandkumar, et al., "Tumour immunomodulation: mucins in resistance to initiation and maturation of immune response against tumours", Scand J Immunol 78(1), 1-7 (2013).
Callahan, MK, et al., "At the bedside: CTLA-4- and PD-1-blocking antibodies in cancer immunotherapy", J Leukoc Biol 94(1), 41-53 (2013).
Candolfi, M., et al., "Release of HMGB1 in response to proapoptotic glioma killing strategies: efficacy and neurotoxicity", Clin Cancer Res 15(13), 4401-4414 (2009).
Chen, D, et al., "Synthetic peptides from the N-terminal regions of CD200 and CD200R1 modulate immunosuppressive and anti-inflammatory effects of CD200-CD200R1 interaction", International Immunology 17(3), 289-296 (2005).
Chitnis, T., et al., "Elevated neuronal expression of CD200 protects Wlds mice from inflammation-mediated neurodegeneration", Am J Pathol 170(5), 1695-1712 (2007).

(Continued)

*Primary Examiner* — Bao Q Li
(74) *Attorney, Agent, or Firm* — Viksnins Harris Padys Malen LLP

(57) ABSTRACT

The present invention in certain embodiments provides a method of inhibiting PD-1 in a cell by administering a CD200 activation receptor ligand (CD200AR-L) to the cell. The present invention in certain embodiments provides a method of enhancing efficacy of a tumor lysate vaccine in a mammal comprising administering a CD200 activation receptor ligand (CD200AR-L) to the mammal prior to the administration of the tumor lysate vaccine.

16 Claims, 18 Drawing Sheets
Specification includes a Sequence Listing.

(56) References Cited

OTHER PUBLICATIONS

Curran, MA, et al., "PD-1 and CTLA-4 combination blockade expands infiltrating T cells and reduces regulatory T and myeloid cells within B16 melanoma tumors", Proc Natl Acad Sci 107(9), 4275-4280 (2010).

Curtin, JF, et al., "Fms-like tyrosine kinase 3 ligand recruits plasmacytoid dendritic cells to the brain", J Immunol 176(6), 3566-3577 (2006).

Curtin, JF, et al., "HMGB1 mediates endogenous TLR2 activation and brain tumor regression", PLoS Med 6(1), e10, (2009).

Curtin, JF, et al., "Treg depletion inhibits efficacy of cancer immunotherapy: implications for clinical trials", PLoS One 3(4), e1983 (2008).

Donson, AM, et al., "Immune gene and cell enrichment is associated with a good prognosis in ependymoma", J Immunol 183(11), 7428-7440 (2009).

Forde, PM, et al., "New strategies in lung cancer: epigenetic therapy for non-small cell lung cancer", Clin Cancer Res 20(9), 2244-2248 (2014).

Ghulam, Muhammad AK, et al., "Antiglioma immunological memory in response to conditional cytotoxic/immune-stimulatory gene therapy: humoral and cellular immunity lead to tumor regression", Clin Cancer Res 15(19), 6113-6127 (2009).

Gorczynski, et al., "Augmented Induction of CD4+CD25+ Treg using monoclonal antibodies to CD200R", Transplantation 79(9), 1180-1183 (2005).

Gorczynski, R., et al., "CD200 is a ligand for all members of the CD200R family of immunoregulatory molecules", J Immunol 172 (12), 7744-7749 (2004).

Gorczynski, Reg, et al., "Peptides of CD200 Modulate LPS-Induced TNF-alpha induction and mortality in vivo", Journal of Surgical Research 145, 87-96 (2008).

Gorczynski, et al., "Receptor engagement on cells expressing a ligand for the tolerance-inducing molecule OX2 induces an immunoregulatory population that inhibits alloreactivity in vitro and in vivo", J Immunol 165 (9), 4854-4860 (2000).

Gorczynski, R.M., "Review Article, CD200:CD200R-Mediated Regulation of Immunity", International Scholarly Research Network, ISRN Immunology, vol. 2012, Article ID 682168, 18 pages (2012).

Gorczynski, et al., "Structural and functional heterogeneity in the CD200R family of immunoregulatory molecules and their expression at the feto-maternal interface", Am J Reprod Immunol 52(2), 147-163 (2004).

Hoek, RM, et al., "Down-regulation of the macrophage lineage through interaction with OX2 (CD200)", Science 290 (5497), 1768-1771 (2000).

Hoffman, LM, et al., "Molecular sub-group-specific immunophenotypic changes are associated with outcome in recurrent posterior fossa ependymoma", Acta Neuropathol 127(5), 731,745 (2014).

Holmannova, et al., "CD200/CD200R paired potent inhibitory molecules regulating immune and inflammatory responses; Part I: CD200/CD200R structure, activation, and function", Acta Medica 55(1), 12-7 (2012).

Inaba, K, et al., "Generation of large numbers of dendritic cells from mouse bone marrow cultures supplemented with granulocyte/macrophage colony-stimulating factor", J Exp Med 176(6), 1693-1702 (1992).

Janne, PA, "Ongoing first-line studies of epidermal growth factor receptor tyrosine kinase inhibitors in select patient populations", Semin Oncol. 32 (6 Suppl 10), S9-15 (2005).

Kawasaki, BT, et al., "Co-expression of the toleragenic glycoprotein, CD200, with markers for cancer stem cells", Biochem Biophys Res Commun 364(4), 778-782 (2007).

Kerkar, SP, et al., "Cellular constituents of immune escape within the tumor microenvironment", Cancer Res 72(13), 3125-3130 (2012).

King, GD, et al., "Flt3L and TK gene therapy eradicate multifocal glioma in a syngeneic glioblastoma model", Neuro Oncol 10(1), 19-31 (2008).

Kirkwood, JM, et al., "Immunotherapy of cancer in 2012", Cancer J Clin 62(5), 309-335 (2012).

Kong, S, et al., "Suppression of human glioma xenografts with second-generation IL13R-specific chimeric antigen receptor-modified T cells", Clin Cancer Res 18(21), 5949-5960 (2012).

Koning, N, et al., "Distribution of the immune inhibitory molecules CD200 and CD200R in the normal central nervous system and multiple sclerosis lesions suggests neuron-glia and glia-glia interactions", J Neuropathol Exp Neurol 68(2), 159-167 (2009).

Koning, N., et al., "Downregulation of macrophage inhibitory molecules in multiple sclerosis lesions", Ann Neurol 62(5), 504-514 (2007).

Kretz-Rommel, Anke, et al., "Blockade of CD200 in the Presence or Absence of Antibody Effector Function: Implications for Anti-CD200 Therapy", Journal of Immunology 180 (2), 699-705 (2008).

Kunkel, T, "Rapid and efficient site specific mutagenesis without phenotypic selection", Proc. Natl Acad Sci vol. 82, 488-492 (1985).

Kunkel, T, et al., "Rapid and Efficient Site-Specific Mutagenesis without Phenotypic Selection", Meth Enzymol 154, 367-382 (1987).

Li, Y, et al., "Aberrant CD200/CD200R1 expression and function in systemic lupus erythematosus contributes to abnormal T-cell responsiveness and dendritic cell activity", Arthritis Res Ther 14 (3), R123 (2012).

Mantovani, A., et al., "Tumor-associated macrophages and the related myeloid-derived suppressor cells as a paradigm of the diversity of macrophage activation", Hum Immunol 70(5), 325-330 (2009).

McGhee, J, et al., "New Perspectives in Mucosal Immunity with Emphasis on Vaccine Development", Seminars in Hematology, vol. 30 (4), Suppl 4, 3-15 (1993).

Mesias, E, et al., "Use of CD200 blockade inhibitor to enhance glioma immunotherapy", Journal Immunotherapy of Cancer 3(2), p. 38 (2015).

Moertel, C, et al., "CD200 in CNS tumor-induced immunosuppression: the role for CD200 pathway blockade in targeted immunotherapy", Journal for Immunotherapy of Cancer 2(1), 10 pages (2014).

Murdoch, C., et al., "The role of myeloid cells in the promotion of tumour angiogenesis", Nat Rev Cancer 8, 618-631 (2008).

Ohlfest, JR, et al., "Vaccine injection site matters: qualitative and quantitative defects in CD8 T cells primed as a function of proximity to the tumor in a murine glioma model", J Immunol 190(2), 613-620 (2013).

Okada, H., et al., "Induction of CD8+ T-cell responses against novel glioma-associated antigen peptides and clinical activity by vaccinations with {alpha}—type 1 polarized dendritic cells and polyinosinic-polycytidylic acid stabilized by lysine and carboxymethylcellulose in p", J Clin Oncol 29(3), 330-336 (2011).

Olin, MR, et al., "Oxygen is a master regulator of the immunogenicity of primary human glioma cells", Cancer Res 71 (21), 6583-6589 (2011).

Olin, MR, et al., "Superior efficacy of tumor cell vaccines grown in physiologic oxygen", Clin Cancer Res 16(19), 4800-4808 (2010).

Olin, M, et al., "Treatment Combining CD200 Immune Checkpoint Inhibitor and Tumor-Lysate Vaccination after Surgery for Pet Dogs with High-Grade Glioma", Cancers 11 (137), 11 pages (2019).

Olin, M., et al., "Vaccination with dendritic cells loaded with allogeneic brain tumor cells for recurrent malignant brain tumors induces a CD4(+)IL17(+) response", J Immunother Cancer 2, 4 (2014).

Patent Cooperation Treaty, International Searching Authority, Search Report and Written Opinion for PCT/US2020/013349, 14 pages, dated May 20, 2020.

Petermann, KB, et al., "CD200 is induced by ERK and is a potential therapeutic target in melanoma", J Clin Invest 117 (12), 3922-3929 (2007).

Prins, RM, et al., "Gene expression profile correlates with T-cell infiltration and relative survival in glioblastoma patients vaccinated with dendritic cell immunotherapy", Clin Cancer Res 17(6), 1603-1615 (2011).

(56) References Cited

OTHER PUBLICATIONS

Puntel, M., et al., "Gene transfer into rat brain using adenoviral vectors", Curr Protoc Neurosci Chapt 4, Unit 4.24 (2010).

Ramaswamy, V., et al., "Recurrence patterns across medulloblastoma subgroups: an integrated clinical and molecular analysis", Lancet Oncol 14(12), 1200-1207 (2013).

Schroeder, K., et al., "Children are not just little adults: recent advances in understanding of diffuse intrinsic pontine glioma biology", Pediatric Research 75, 205-209 (2013).

Southgate, T., et al., "Gene transfer into neural cells in vitro using adenoviral vectors", Curr Protoc Neurosci, Chapter 4, Unit 4.23 (2008).

Stupp, R., et al., "Effects of radiotherapy with concomitant and adjuvant temozolomide versus radiotherapy alone on survival in glioblastoma in a randomised phase III study: 5-year analysis of the EORTC-NCIC trial", Lancet Oncol 10(5), 459-466 (2009).

Stupp, R., et al., "Radiotherapy plus concomitant and adjuvant temozolomide for glioblastoma", N Engl J Med 352, 987-996 (2005).

Walker, DG, et al., "Decreased expression of CD200 and CD200 receptor in Alzheimer's disease: a potential mechanism leading to chronic inflammation", Exp Neurol 215(1), 5-19 (2009).

Weber, J., "Immune checkpoint proteins: a new therapeutic paradigm for cancer—preclinical background: CTLA-4 and PD-1 blockade", Semin Oncol 37(5), 430-439 (2010).

Wick, DA, et al., "Profound CD8+ T cell immunity elicited by sequential daily immunization with exogenous antigen plus the TLR3 agonist poly(I:C)", Vaccine 29 (5), 984-993 (2011).

Witt, H., et al., "Delineation of two clinically and molecularly distinct subgroups of posterior fossa ependymoma", Cancer Cell 20(2), 143-157 (2011).

Wong, KK, et al., "Soluble CD200 is critical to engraft chronic lymphocytic leukemia cells in immunocompromised mice", Cancer Res 72(19), 4931-4943 (2012).

Wright, et al., "Characterization of the CD200 receptor family in mice and humans and their interactions with CD200", J Immunol 171(6), 3034-3046 (2003).

Xiong, Z, et al., "CD200 Checkpoint Reversal: A Novel Approach to Immunotherapy", Clinical Cancer Research 26 (1), 232-241 (2019).

Xiong, Z., et al., "Effective CpG immunotherapy of breast carcinoma prevents but fails to eradicate established brain metastasis", Clin Cancer Res 14(17), 5484-5493 (2008).

Xiong, Z, et al., "Tumor-derived vaccines containing CD200 inhibit immune activation: implications for immunotherapy", Immunotherapy 8(9), 1059-1071 (2016).

Coles, S, et al., "The immunosuppressive ligands PD-L1 and CD200 are linked in AML T-cell immunosuppression: identification of a new immunotherapeutic synapse", Leukemia 29, 1952-1954 (2015).

* cited by examiner

Figure 2A

```
                                      Human and murine P1    Human P3
Canine  -VVTQDEKRLLNTPASLRCSLQNPEEVLIVTWQKVKPVSLENMVTFSKNHGVVVQPAYKD  118
Human   QVVTQDEREQLYTPASLKCSLQNAQEALIVTWQKKKAVSPENMVTFSENHGVVIQPAYKD  92
Mouse   EVVTQDERKALHTTASLRCSLKTSQEPLIVTWQKKKAVSPENMVTYSKTHGVVIQPAYKD  92
        :******::  *  * ***:***::  :* ******* * **  *****:*::****:******

Human P2  Human P4 and canine peptide
Canine  KINVTQLELKNSTITFWNTTLEDEGCYKCLFNTFGSGKISGTACLTLSVQPTVFLHYNFF  178
Human   KINITQLGLQNSTITFWNITLEDEGCYMCLFNTFGFGKISGTACLTVYVQPIVSLHYKFS  152
Mouse   RINVTELGLWNSSITFWNTTLEDEGCYMCLFNTFGSQKVSGTACLTYVQPIVHLHYNYF   152
        :**:*:*  * **:***** ******* *******      *:******:  *** * ***:::
```

Figure 2B

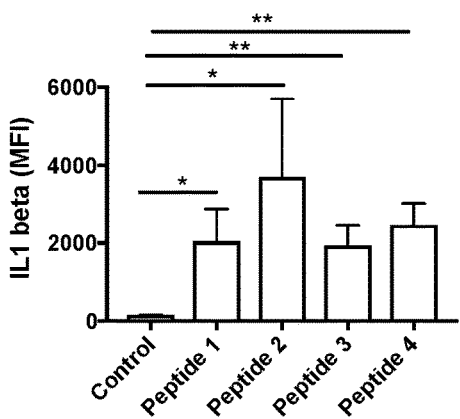

Figure 2C

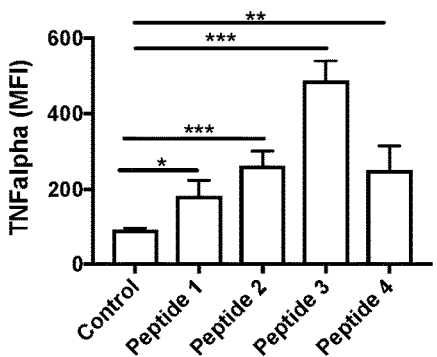

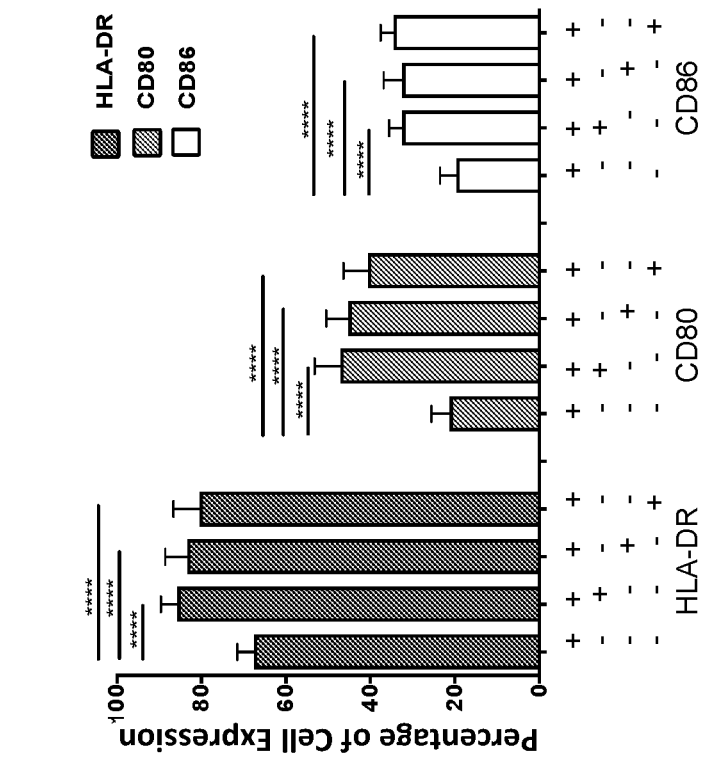
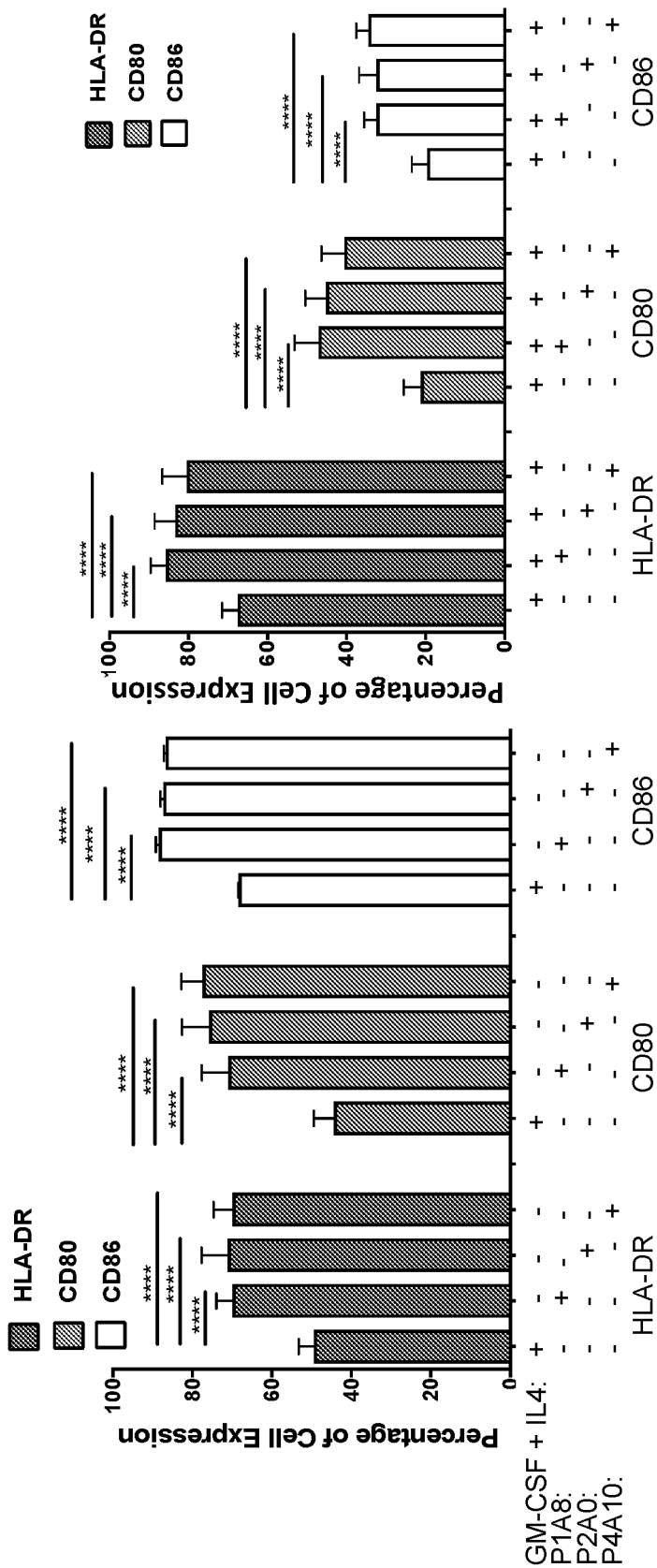
Figure 4A
Figure 4B

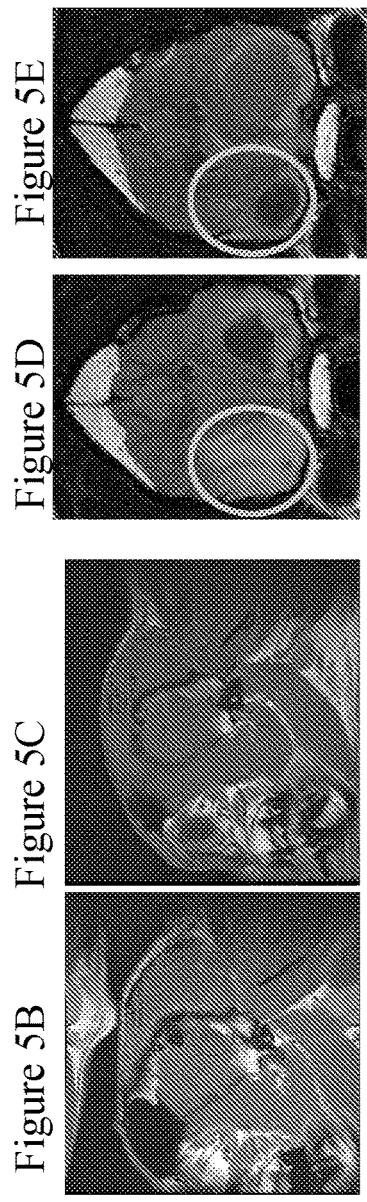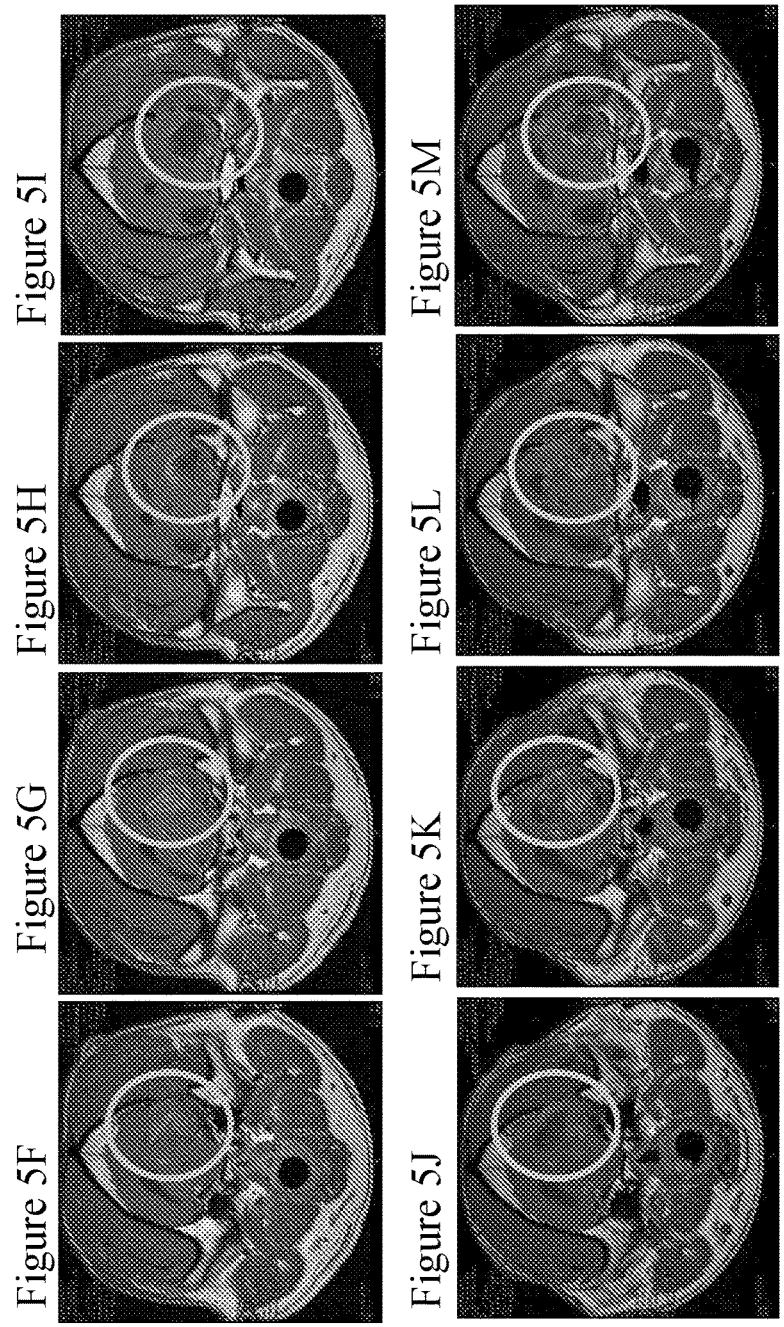

Figure 6E

| Index | Name | P-value | Adjusted p-value | Z-score | Combined score |
|---|---|---|---|---|---|
| 1 | Immune System_Homo sapiens_R-HSA-168256 | 1.116e-49 | 8.886e-47 | -2.23 | 251.61 |
| 2 | Immunoregulatory interactions between a Lymphoid and a non-Lymphoid cell_Homo sapiens_R-HSA-198933 | 4.226e-37 | 1.682e-34 | -2.00 | 167.65 |
| 3 | Extracellular matrix organization_Homo sapiens_R-HSA-1474244 | 1.460e-29 | 3.875e-27 | -2.10 | 139.12 |
| 4 | Adaptive Immune System_Homo sapiens_R-HSA-1280218 | 2.066e-21 | 3.290e-19 | -2.25 | 107.12 |
| 5 | Class A/1 (Rhodopsin-like receptors)_Homo sapiens_R-HSA-373076 | 9.042e-21 | 1.200e-18 | -2.10 | 96.97 |
| 6 | Chemokine receptors bind chemokines_Homo sapiens_R-HSA-380108 | 2.178e-22 | 4.334e-20 | -1.93 | 96.39 |
| 7 | Cytokine Signaling in Immune system_Homo sapiens_R-HSA-1280215 | 5.330e-17 | 6.061e-15 | -2.35 | 88.11 |
| 8 | GPCR ligand binding_Homo sapiens_R-HSA-500792 | 1.172e-15 | 1.166e-13 | -2.20 | 75.57 |
| 9 | Innate Immune System_Homo sapiens_R-HSA-168249 | 1.917e-13 | 1.272e-11 | -2.33 | 68.28 |
| 10 | Peptide ligand-binding receptors_Homo sapiens_R-HSA-375276 | 1.771e-15 | 1.566e-13 | -1.91 | 64.80 |

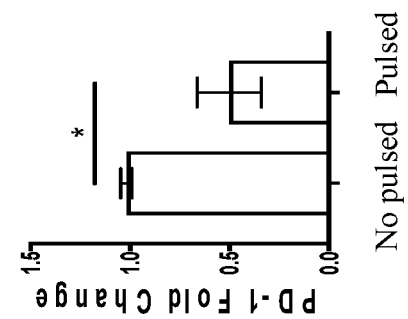
Fig. 7A. mCD200R1 (APC)
Fig. 7B mPD-1 (APC)
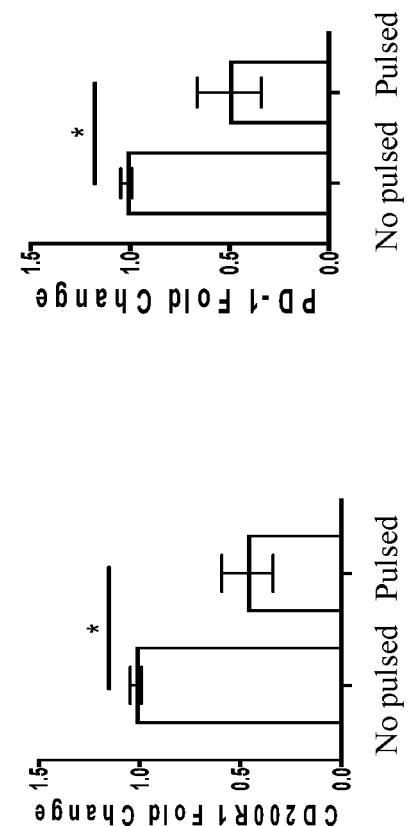
Fig. 7C. mCD200R1 (T-cells)
Fig. 7D. hPD-1 (T-cells)
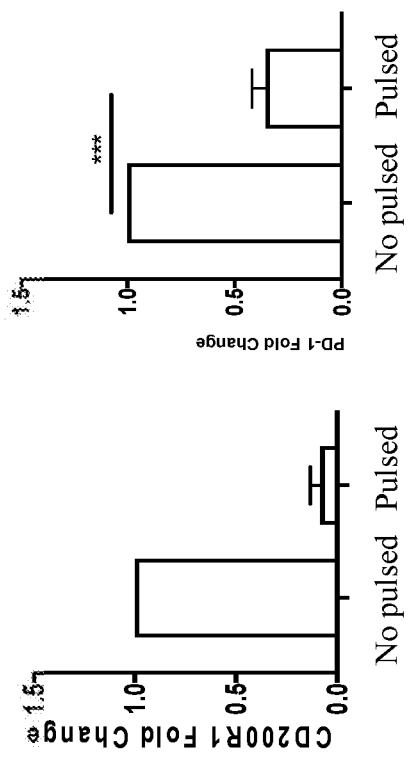
Fig. 7E. hCD200R1
Fig. 7F. hCD200R1
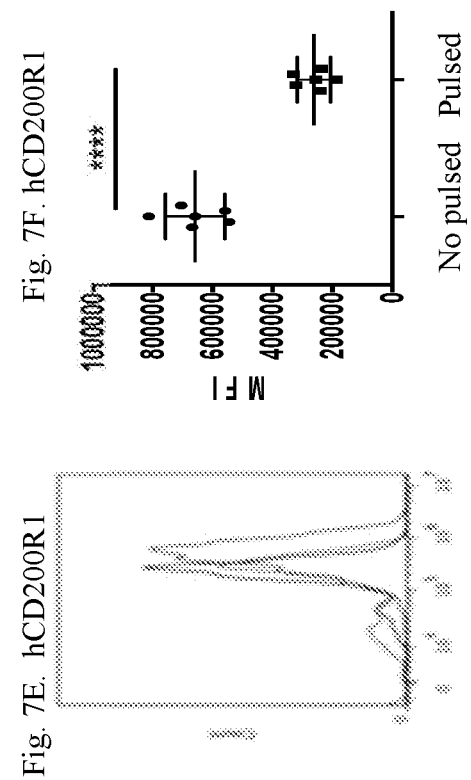
Fig. 7G. hPD-1

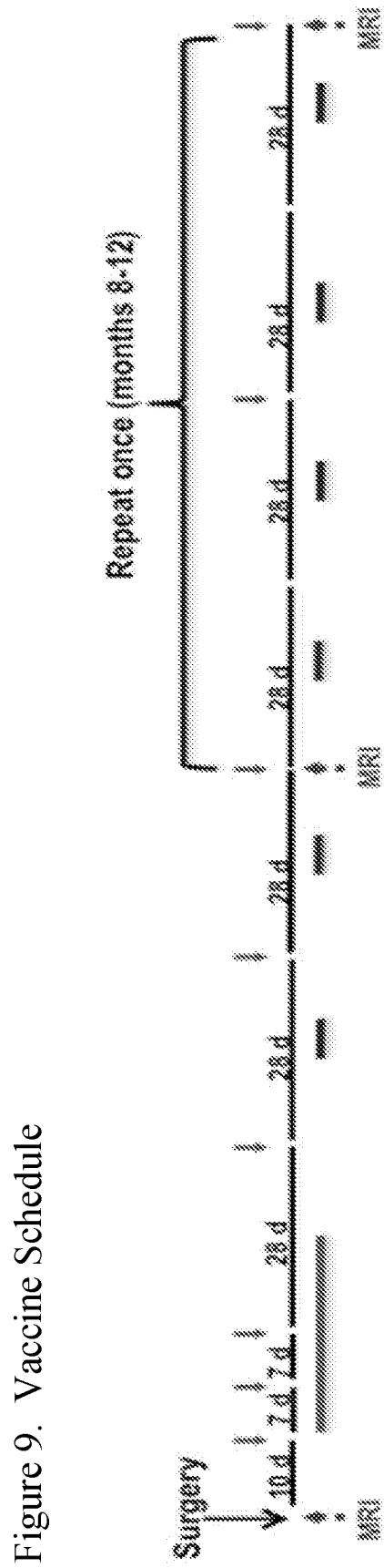
Figure 9. Vaccine Schedule

Figure 10. Experimental Model
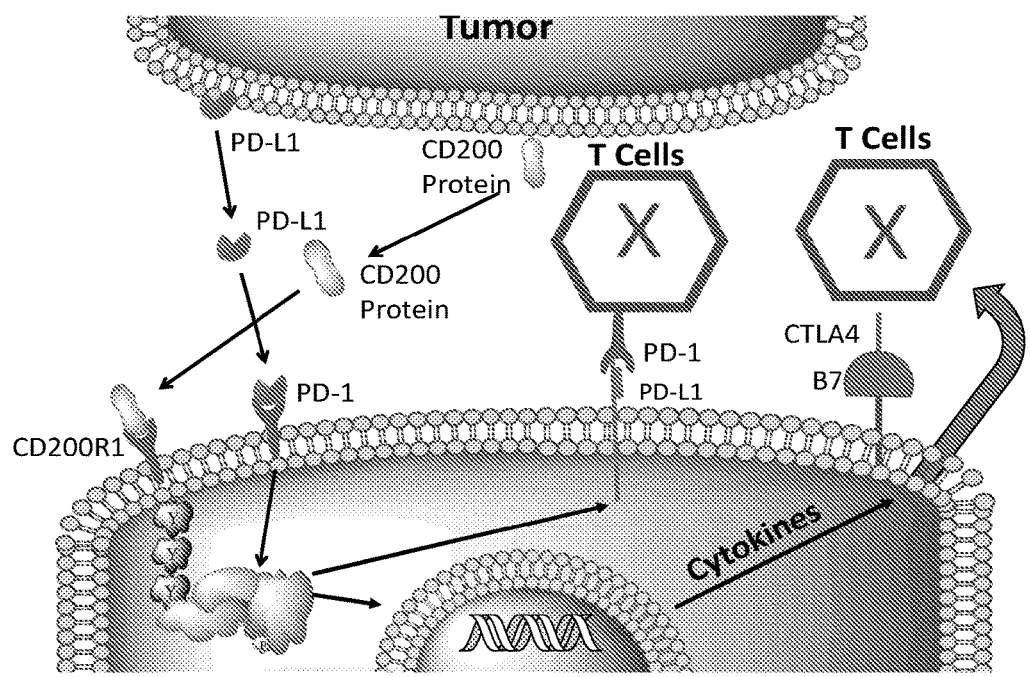
Figures 11A-11C
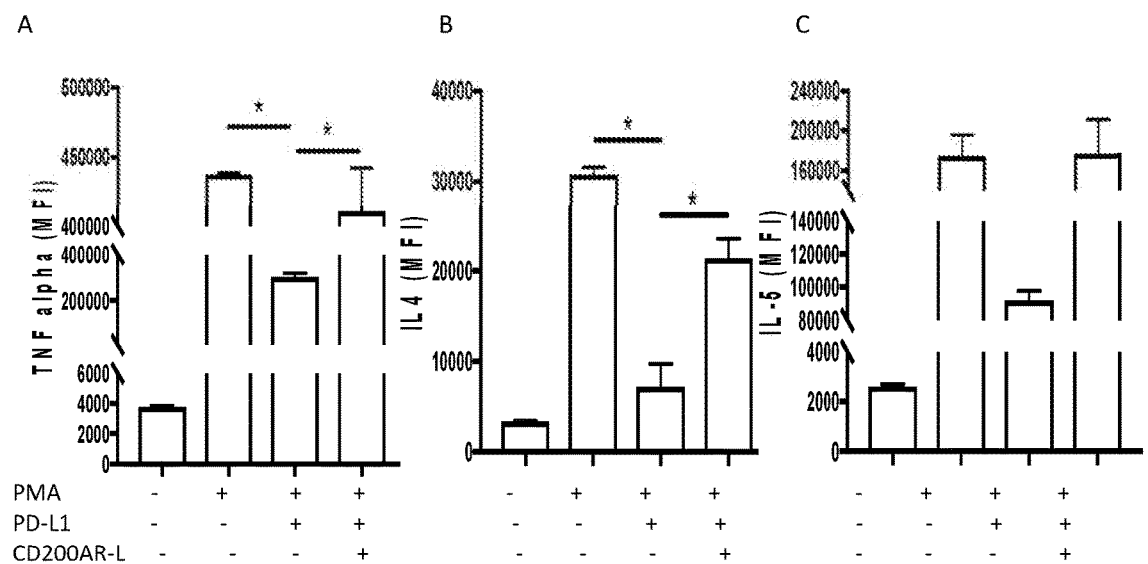

A.

B.

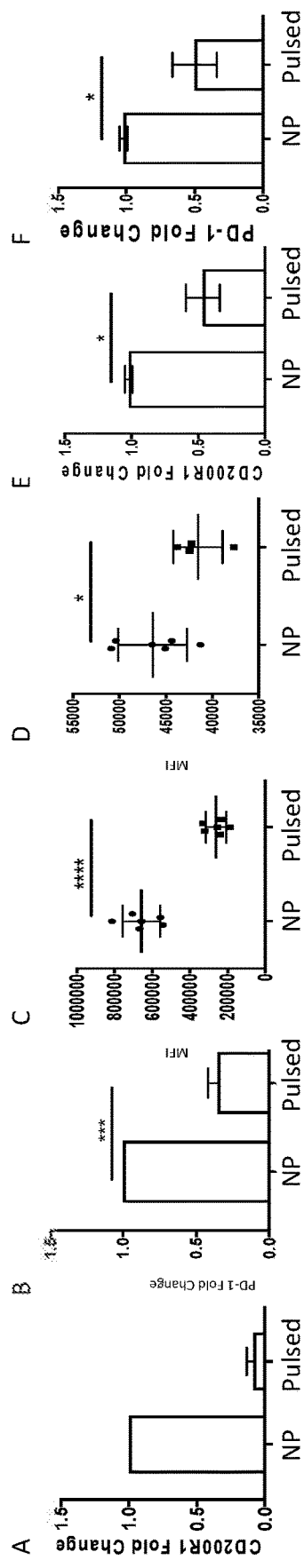
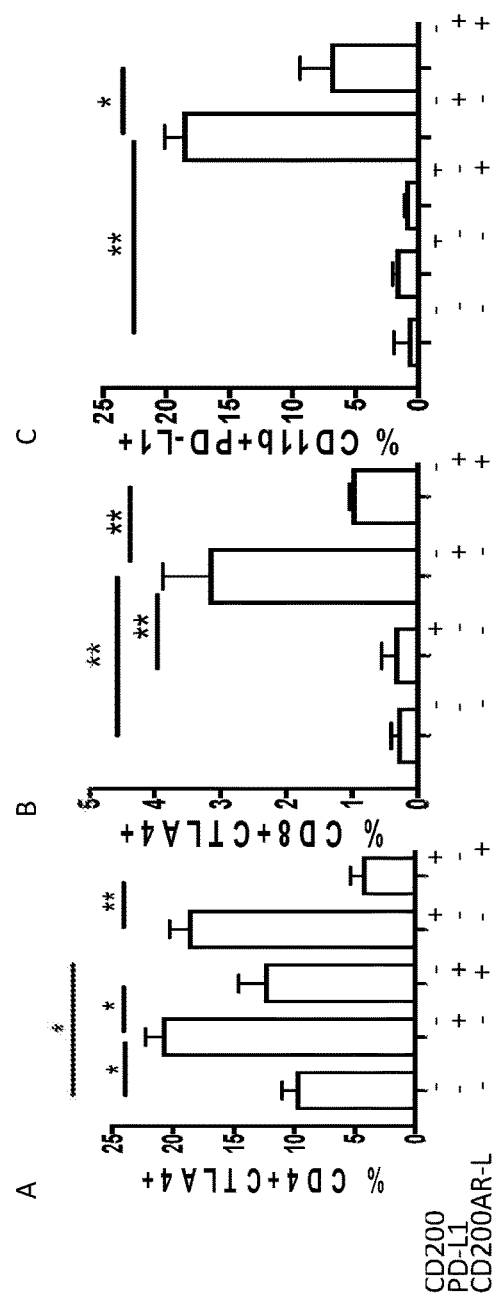
Figures 13A-13F
Figures 14A-14C

SEQUENCE LISTING

```
<160> NUMBER OF SEQ ID NOS: 18

<210> SEQ ID NO 1
<211> LENGTH: 15
<212> TYPE: PRT
<213> ORGANISM: Homo sapiens

<400> SEQUENCE: 1

Ile Val Thr Trp Gln Lys Lys Lys Ala Val Ser Pro Glu Asn Met
1               5                   10                  15

<210> SEQ ID NO 2
<211> LENGTH: 15
<212> TYPE: PRT
<213> ORGANISM: Homo sapiens

<400> SEQUENCE: 2
```

```
Asn Ile Thr Leu Glu Asp Glu Gly Cys Tyr Met Cys Leu Phe Asn
1               5                   10                  15

<210> SEQ ID NO 3
<211> LENGTH: 15
<212> TYPE: PRT
<213> ORGANISM: Homo sapiens

<400> SEQUENCE: 3

Val Thr Phe Ser Glu Asn His Gly Val Val Ile Gln Pro Ala Tyr
1               5                   10                  15

<210> SEQ ID NO 4
<211> LENGTH: 15
<212> TYPE: PRT
<213> ORGANISM: Homo sapiens

<400> SEQUENCE: 4

Cys Leu Phe Asn Thr Phe Gly Phe Gly Lys Ile Ser Gly Thr Ala
1               5                   10                  15

<210> SEQ ID NO 5
<211> LENGTH: 15
<212> TYPE: PRT
<213> ORGANISM: Canis lupus

<400> SEQUENCE: 5

Cys Leu Phe Asn Thr Phe Gly Ser Gly Lys Ile Ser Gly Thr Ala
1               5                   10                  15

<210> SEQ ID NO 6
<211> LENGTH: 15
<212> TYPE: PRT
<213> ORGANISM: Homo sapiens

<400> SEQUENCE: 6

Ile Val Thr Trp Gln Lys Lys Ala Ala Val Ser Pro Glu Asn Met
1               5                   10                  15

<210> SEQ ID NO 7
<211> LENGTH: 15
<212> TYPE: PRT
<213> ORGANISM: Homo sapiens

<400> SEQUENCE: 7

Asn Ile Thr Leu Glu Asp Glu Gly Cys Tyr Met Cys Leu Phe Asn
1               5                   10                  15

<210> SEQ ID NO 8
<211> LENGTH: 15
<212> TYPE: PRT
<213> ORGANISM: Homo sapiens

<400> SEQUENCE: 8

Asn Ile Thr Leu Ala Asp Glu Gly Cys Tyr Met Cys Leu Phe Asn
1               5                   10                  15

<210> SEQ ID NO 9
<211> LENGTH: 15
<212> TYPE: PRT
<213> ORGANISM: Homo sapiens

<400> SEQUENCE: 9

Val Thr Phe Ser Glu Asn His Gly Val Val Ile Ala Pro Ala Tyr
```

-continued

```
1               5                   10                  15
```

<210> SEQ ID NO 10
<211> LENGTH: 15
<212> TYPE: PRT
<213> ORGANISM: Homo sapiens

<400> SEQUENCE: 10

Cys Leu Phe Asn Thr Phe Gly Phe Gly Ala Ile Ser Gly Thr Ala
1               5                   10                  15

<210> SEQ ID NO 11
<211> LENGTH: 119
<212> TYPE: PRT
<213> ORGANISM: Canis lupus

<400> SEQUENCE: 11

Val Val Thr Gln Asp Glu Lys Arg Leu Leu Asn Thr Pro Ala Ser Leu
1               5                   10                  15

Arg Cys Ser Leu Gln Asn Pro Glu Glu Val Leu Ile Val Thr Trp Gln
                20                  25                  30

Lys Val Lys Pro Val Ser Leu Glu Asn Met Val Thr Phe Ser Lys Asn
            35                  40                  45

His Gly Val Val Gln Pro Ala Tyr Lys Asp Lys Ile Asn Val Thr
        50                  55                  60

Gln Leu Glu Leu Lys Asn Ser Thr Ile Thr Phe Trp Asn Thr Thr Leu
65                  70                  75                  80

Glu Asp Glu Gly Cys Tyr Lys Cys Leu Phe Asn Thr Phe Gly Ser Gly
                85                  90                  95

Lys Ile Ser Gly Thr Ala Cys Leu Thr Leu Ser Val Gln Pro Thr Val
            100                 105                 110

Phe Leu His Tyr Asn Phe Phe
        115

<210> SEQ ID NO 12
<211> LENGTH: 120
<212> TYPE: PRT
<213> ORGANISM: Homo sapiens

<400> SEQUENCE: 12

Gln Val Val Thr Gln Asp Glu Arg Glu Gln Leu Tyr Thr Pro Ala Ser
1               5                   10                  15

Leu Lys Cys Ser Leu Gln Asn Ala Gln Glu Ala Leu Ile Val Thr Trp
                20                  25                  30

Gln Lys Lys Lys Ala Val Ser Pro Glu Asn Met Val Thr Phe Ser Glu
            35                  40                  45

Asn His Gly Val Val Ile Gln Pro Ala Tyr Lys Asp Lys Ile Asn Ile
        50                  55                  60

Thr Gln Leu Gly Leu Gln Asn Ser Thr Ile Thr Phe Trp Asn Ile Thr
65                  70                  75                  80

Leu Glu Asp Glu Gly Cys Tyr Met Cys Leu Phe Asn Thr Phe Gly Phe
                85                  90                  95

Gly Lys Ile Ser Gly Thr Ala Cys Leu Thr Val Tyr Val Gln Pro Ile
            100                 105                 110

Val Ser Leu His Tyr Lys Phe Ser
        115                 120

<210> SEQ ID NO 13
```

```
<211> LENGTH: 120
<212> TYPE: PRT
<213> ORGANISM: Mus musculus

<400> SEQUENCE: 13

Glu Val Val Thr Gln Asp Glu Arg Lys Ala Leu His Thr Thr Ala Ser
1               5                   10                  15

Leu Arg Cys Ser Leu Lys Thr Ser Gln Glu Pro Leu Ile Val Thr Trp
            20                  25                  30

Gln Lys Lys Lys Ala Val Ser Pro Glu Asn Met Val Thr Tyr Ser Lys
        35                  40                  45

Thr His Gly Val Val Ile Gln Pro Ala Tyr Lys Asp Arg Ile Asn Val
    50                  55                  60

Thr Glu Leu Gly Leu Trp Asn Ser Ser Ile Thr Phe Trp Asn Thr Thr
65                  70                  75                  80

Leu Glu Asp Glu Gly Cys Tyr Met Cys Leu Phe Asn Thr Phe Gly Ser
                85                  90                  95

Gln Lys Val Ser Gly Thr Ala Cys Leu Thr Leu Tyr Val Gln Pro Ile
            100                 105                 110

Val His Leu His Tyr Asn Tyr Phe
        115                 120

<210> SEQ ID NO 14
<211> LENGTH: 8
<212> TYPE: PRT
<213> ORGANISM: Gallus gallus

<400> SEQUENCE: 14

Ser Ile Ile Asn Phe Glu Lys Leu
1               5

<210> SEQ ID NO 15
<211> LENGTH: 14
<212> TYPE: PRT
<213> ORGANISM: Mus musculus

<400> SEQUENCE: 15

Val Thr Trp Gln Lys Lys Lys Ala Val Ser Pro Ala Asn Met
1               5                   10

<210> SEQ ID NO 16
<211> LENGTH: 15
<212> TYPE: PRT
<213> ORGANISM: Canis lupus

<400> SEQUENCE: 16

Cys Leu Phe Asn Thr Phe Gly Ser Gly Ala Ile Ser Gly Thr Ala
1               5                   10                  15

<210> SEQ ID NO 17
<211> LENGTH: 14
<212> TYPE: PRT
<213> ORGANISM: Mus musculus

<400> SEQUENCE: 17

Val Thr Trp Gln Lys Lys Lys Ala Val Ser Pro Glu Asn Met
1               5                   10

<210> SEQ ID NO 18
<211> LENGTH: 9
<212> TYPE: PRT
<213> ORGANISM: Cytomegalovirus
```

```
<400> SEQUENCE: 18

Asn Leu Val Pro Met Val Ala Thr Val
1               5
```

CD200AR LIGANDS FOR CANCER IMMUNOTHERAPY

CROSS-REFERENCE TO RELATED APPLICATION

This application claims priority to U.S. Provisional Application No. 62/792,311, filed Jan. 14, 2019. The entire content of the application referenced above is hereby incorporated by reference herein.

SEQUENCE LISTING

The instant application contains a Sequence Listing which has been submitted in ASCII format via EFS-Web and is hereby incorporated by reference in its entirety. The ASCII copy, created on Mar. 12, 2020, is named 09531_481WO1_SL.txt and is 6.14 bytes in size.

BACKGROUND

Despite advances in cancer research, there are still no adequate treatments for many cancers. For example, malignant glioma is a devastating disease that arises in over 14,000 patients a year in the United States. Due to the ability of glioma cells to migrate several centimeters from the bulk tumor cavity, current standard of care only results in marginal improvements, with a 5-year survival below 30%. Patients with glioblastoma exhibit systemic immune suppression resulting in deficient adaptive immune responses. These deficiencies' are due to the enriched immunosuppressive factors secreted by the tumor suppressing T cell proliferation and cytotoxic function. Immunosuppression plays an important role in tumor progression in patients with glioblastoma. If the immune suppression could be reversed allowing an effective immune targeting, then patients with glioma will have less tumor progression and improved outcomes.

Accordingly, new compositions and methods to treat cancer are needed. In particular, new compositions that reverse the immunologically suppressed microenvironment caused by tumors are needed.

SUMMARY

The present invention in certain embodiments provides a method of inhibiting PD-1 in a cell by administering a CD200 activation receptor ligand (CD200AR-L) to the cell. In certain embodiments, the CD200AR-L is peptidomimetic. In certain embodiments, the peptidomimetic comprises one or more D-isomer amino acids. In certain embodiments, the peptidomimetic comprises one or more unnatural amino acids.

The present invention in certain embodiments provides a method of enhancing efficacy of a tumor lysate vaccine in a mammal comprising administering a CD200 activation receptor ligand (CD200AR-L) to the mammal prior to the administration of the tumor lysate vaccine. In certain embodiments, the tumor lysate is substantially devoid of CD200. As used herein "substantially devoid" means that the substance (e.g., tumor lysate) has a diminished level of CD200, e.g., between 1-100% less CD200 than an unprocessed substance. In certain embodiments, the CD200 is removed by absorption using standard methods.

BRIEF DESCRIPTION OF DRAWINGS

FIGS. 2A-2D. Targeting CD200 activation receptors stimulates antigen-presenting cells. (FIG. 2A) Canine CD200 (aa 60-178) (SEQ ID NO: 11), Human CD200 (aa 33-152) (SEQ ID NO: 12), and Murine CD200 (aa 33-152) (SEQ ID NO: 13) sequences showing the homology of the different CD200 peptides. Canine P4 is sequences 147-161 of SEQ ID NO: 11. Human P1 is sequences 61-75 of SEQ ID NO: 12; Human P2 is sequences 110-124 of SEQ ID NO: 12; Human P3 is sequences 76-90 of SEQ ID NO: 12; and Human P4 is sequences 121-135 of SEQ ID NO: 12. Murine P1 is sequences 62-75 of SEQ ID NO:13.

(FIGS. 2B, 2C) CD14$^+$ cells from healthy donors were pulsed with human peptides P1 (IVTWQKKKAVSPENM) (SEQ ID NO: 1), P2 (NITLEDEGCYMCLFN) (SEQ ID NO: 2), P3 (VTFSENHGVVIQPAY) (SEQ ID NO: 3) or P4 (CLFNTFGFGKISGTA) (SEQ ID NO: 4) and incubated for 48 h. Cells that were not pulsed (NP) were used as controls. Supernatants were harvested and analyzed for IL1β (FIG. 2B) and TNFα (FIG. 2C). (FIG. 2D) Immature dendritic cells were pulsed with the CMV antigen pp65±P1-P4. The cells were washed, and autologous T-cells from CMV-positive and CMV-negative healthy donors were added back and incubated for a further 48 h. Supernatants were harvested and analyzed for IFNα production. Error bars represent standard deviation (n=3/group *P<0.05, P<0.005, *P<0.0005; by t-test, and *P<0.05 by two-way ANOVA). Data represent three separate healthy donors in each group.

(FIG. 3A) CD14$^+$ cells were pulsed with equal molar ratio of peptides, and incubated for 48 hrs. Supernatants were harvested and analyzed for IFN-1β, IL-12p70, MIG, and TNFα content. (FIG. 3B) In separate experiments, cells were incubated for 1 h. RNA was harvested and analyzed by NanoSight for immune-related transcription alterations. Pulsed cells were normalized to a non-pulsed (NP) control to derive the heat map, which was created by using Java Treeview within nSolver. Cluster analysis of the 35 genes examined showed significant P1A8 (IVTWQKKAAVSPENM) (SEQ ID NO: 6), P2A0 (NITLEDEGCYMCLFN) (SEQ ID NO: 7), P2A5 (NITLADEGCYMCLFN) (SEQ ID NO: 8), P3A12 (VTFSENHGVVIAPAY) (SEQ ID NO: 9), and P4A10 (CLFNTFGFGAISGTA) (SEQ ID NO: 10) expression changes in one or more of the treated samples when compared to the NP controls. D1-P3A12 was an outlier and was excluded from the analysis. Error bars represent standard deviation (n=3/group; *P<0.05, P<0.005, *P<0.0005 by t-test, and *P<0.05 by two-way ANOVA).

FIGS. 4A-4D. Targeting CD200 activation receptors enhances dendritic cell maturation. (FIGS. 4A, 4B) CD14 purified cells were pulsed with (FIG. 4A) GM-CSF+IL4 or equal molar ratios of peptides P1A8, P2A0, or P4A10 or (FIG. 4B) GM-CSF+IL4 plus equal molar ratios of peptides P1A8, P2A0, or P4A10 and incubated for 48 h. Cells were harvested and phenotyped for CD80, CD86, and HLA-DR.

(FIG. 4C) Immature dendritic cells from donors with or without CMV were pulsed with the CMV antigen pp65+/− equal molar ratios of peptides P1A8, P2A0, or P4A10. Cells were washed, and autologous T-cells were added back and incubated for a further 48 h. Supernatants were analyzed for IFNγ production. (FIG. 4D) Immature dendritic cells were pulsed with the CMV antigen pp65+/−P4A10. After the cells were washed, autologous T-cells were added back and incubated for a further 48 h. Supernatants were analyzed for IFNγ, IL-6, TNFα and RANTES content. Error bars represent standard deviation (n=3 healthy donors/group, *P<0.05, P<0.005, *P<0.0005 by t-test). The data represent three separate healthy donors. Black bars represent CMV-negative donors.

(FIG. 5A) Tumors were resected, and the dogs were vaccinated with autologous tumor lysates and canine-specific CD200AR-L and followed for progression-free survival (black line at top) and overall survival (middle line with arrows). A historical cohort treated with tumor lysate only is shown for comparison (steep line at left). Black arrows represent dogs currently on trial. (FIGS. 5B, 5C) Following resection there was (FIG. 5B) a range of remaining tumors (FIG. 5C) showing regression 4 months post-surgery. (FIGS. 5D, 5E) Images from one of five dogs that developed central leukoencephalopathy characterized by T2 hyperintensity of the periventricular white matter tracts and ventricular dilatation (FIG. 5D), which resolved following corticosteroid treatment (FIG. 5E). (FIG. 5F-5I) However, this dog had a tumor recurrence visible on an MRI performed 2 months after the corticosteroid treatment. (FIG. 5J-5M) Vaccination with CD200AR-L was reinitiated in this dog after recovery, and there was evidence of tumor regression 2 months later after 2 doses of vaccine. (FIG. 5N) The serum CD200 (sCD200) level was significantly associated with overall survival (*p=0.005). Survival groups were analyzed using Mantel-Cox, log-rank test for trend, and Gehan-Breslow-Wilcoxon.

FIGS. 6A-6E. CD200R1-related genes are associated with shorter overall survival in humans. (FIG. 6A) Clusters of genes associated with overall survival were analyzed in patient tumor samples available in The Cancer Genome Atlas database. Gene Cluster Expression Summary Scores were used to identify the clusters identified in the figure by numbers. Those significant in Kaplan-Meier analyses are indicated with symbols and their associated p values are shown. (FIGS. B-6D) Kaplan-Meier (KM) plots showing that patients who expressed high levels of the gene cluster containing CD200 (dashed lines) showed shorter overall survival than those expressing lower levels (solid lines). Comparisons are top quartile (Q1) versus three lowest quartiles (Q234), top two quartiles (Q12) versus the lowest two (Q34), and top three quartiles (Q123) versus the lowest (Q4). FIG. 6E provides a table showing whether CD200-related genes are associated with survival, we analyzed gene expression profiles of patient tumor samples in the TCGA dataset using GCESS. This enabled us to identify clusters of genes that are concordantly expressed across the dataset and are associated with overall survival in an unbiased statistical analysis. CD200R1 expression was found within a large cluster of genes highly enriched in immune-related transcripts. Increased transcript levels of genes in this cluster were significantly associated with decreased survival. Patients who expressed high levels of the CD200R1-containing cluster (cluster 14) showed shorter overall survival times than patients who expressed lower levels of the cluster. These results suggest the critical importance of the CD200/CD200R1 interaction in mediating an immunosuppressive glioblastoma microenvironment.

FIGS. 7A-7G. CD200AR-L pulses down-regulate inhibitory CD200R1. Murine CD11b cells were pulsed with mCD200AR-L, RNA was extracted and analyzed for CD200R1 or PD-1 expression (FIGS. 7A&B). To further these studies, CD11b cells were stimulated with OVA+/− CD200AR-L, cells were washed and purified T cells were added. Following 24 hr incubation, T-cells were isolated and analyzed for CD200R1 or PD-1 expression (FIGS. 7C&D). To see if these experiments translated to humans, CD14 cells were pulsed with our human CD200AR-L. Following 24 hr incubation, cells were stained with anti-CD200R1 analyzed by flow cytometry (FIG. 7E), mean fluorescent intensity was analyzed for CD200R1 (FIG. 7F) and PD-1 (FIG. 7G) expression. These experiments demonstrated targeting the CD200AR downregulates the inhibitor CD200R1 and PD-1 in both murine and human antigen-presenting cells validating that the CD200R1 and PD-1 cross-talk and the inhibitory CD200R1 and PD-1 pathways interconnect with the CD200AR4. Error bars represent standard deviation (n=3/group, *P<0.05, P<0.005, *P<0.0005, ****P<0.00005 by t-test.

FIG. 9. Vaccine Schedule. Surgical debulking and post-operative MRI were performed on day 0. Intradermal (ID) injection of CD200 inhibitor, followed in 6-24 h by imiquimod application and ID injection of a mixture of tumor lysate vaccine+CD200 inhibitor (downward pointing solid arrows), was started on day 10 and repeated once weekly for 3 weeks, then once every 4 weeks for 3 months, then every 8 weeks for 1 year or until tumor recurrence or death. MRI of the brain (upward pointing dashed arrows) was performed immediately after surgery and then every 4 months.

FIG. 10. Experimental model.

FIGS. 11A-11C. Targeting the CD200 activation receptors inhibits the effects of the suppressive PD-L1. Murine splenocytes were activated with PMA, +/−PD-L1 or PD-L1+ mCD200AR-L. Following 48 hr incubation, supernatants were analyzed for (FIG. 11A) TNFα (FIG. 11B) IL-4 or (FIG. 11C) IL-5. Error bars are representative of n=3; *P<0.005.

(FIG. 12A) Wildtype or CD200R1KO macrophage were pulsed with PD-L1 and for analyzed for pSHP; (FIG. 12B) Wildtype of CD200R1KO cells were pulsed with LPS+/−PD-L1. Error bars are representative of n=3 **P<0.001 by t-test.

FIGS. 13A-13F. Figure. Targeting the CD200 activation receptors downregulates CD200R1 and PD-1 expression. Murine CD11b cells were pulsed CD200AR-L and analyzed for transcription levels of (FIG. 13A) CD200R1 and (FIG. 13B) PD-1; Human CD14 cells were pulsed with human CD200AR-L, following 48 hr incubation, cells were analyzed by flow cytometry for (FIG. 13C) CD200R1 and (FIG. 13D) PD-1 expression; murine CD11b cells from wildtype mice were pulsed with OVA+/− the CD200AR-L. Cells were washed, purified CD3 cells were added to CD11b cells for 24 hrs. CD3 cells were purified and analyzed for transcription levels of (FIG. 13E) CD200R1 and (FIG. 13F) PD-1. Error bars are representative of n=3 *P<0.005, P<0.0001 and *P<0.00001.

FIGS. 14A-14C. CD200AR-L overpowers CTLA4 and PD-L1 expression. Splenocytes were pulsed with CD200, PD-L1+/-mCD200AR-L. Cells were analyzed by flow cytometry for the (FIG. 14A) CD4$^+$CTLA4$^+$, (FIG. 14B) CD8$^+$CTLA4$^+$or (FIG. 14C) CD11b$^+$PD-L1$^+$ populations. Error bars are representative of n=2 *P<0.005, **P<0.0001.

DETAILED DESCRIPTION

Figure 1A:
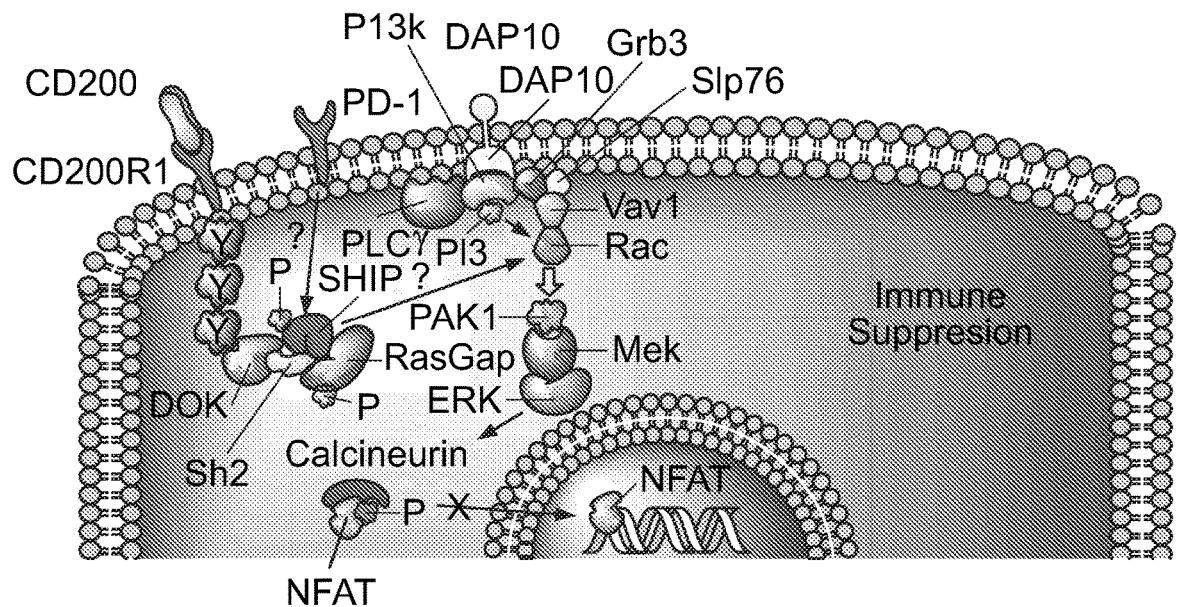
FIGS. 1A and 1B. Experimental model. CD200 and PD-L are secreted from tumor cells binds to the CD200 inhibitory receptor (CD200R1) or PD-1 receptors on antigen-presenting cells, shutting down the immune system. Both the CD200R1 and PD-1 cross talk with each other through the SHIP signaling molecule and interact with the activation receptor-signaling pathway (FIG. 1a). Targeting the CD200 activation with a CD200 inhibitory peptide ligand (CD200AR-L) overpowers the CD200R1 and PD-L pathway by downregulating the CD200AR and PD-1 on immune cells (FIG. 1b). In addition to the inhibitory receptor, CD200 checkpoint has activation receptors that have adjuvant-like properties when stimulated, surmounting the inhibitory signals and activating the immune cell.

The unprecedented success of cancer immunotherapy over the past decade is a direct result of the concept of immune-surveillance, revolutionizing clinical management of malignancies that previously had dismal prognosis. At the forefront of immunotherapy development are immune-checkpoint inhibitors, which have seen enormous and unparalleled success in cancer therapy as a result of their broad bioactivity across many histological tumor types, the durability of their responses, and cures observed even in metastatic and chemoresistant diseases.

Among the immune checkpoint-blocking strategies, the two most prominent (in terms of their clinical success to date) are the targeting of cytotoxic-T-lymphocyte-associated protein 4 (CTLA-4) and the interaction between programmed cell death 1 (PD-1) and programmed cell death ligand 1 (PD-L1). However, due to the multiple mechanisms tumors utilize to inhibit immune response has impeded the use of monotherapy. This is particularly true for malignant brain tumors such as gliomas, both high grade (HGG) and low grade (LGG) as tumors with lower mutational burden and/or lower immunogenicity may be inherently resistant to this form of therapy. Even in favorable tumor types, tumor heterogenicity hinders immunotherapy. This may be related to redundancy in the web of activating and inhibitory molecules targeted by immune checkpoint inhibitors. Therefore, multiple inhibitors have been employed significantly enhancing survival; unfortunately, these therapies often cause serious immune-related adverse events including death. Therefore, alternative approaches to targeting multiple checkpoints is imperative.

Currently, work is focused on single inhibitors against PD-1, PD-L1 and CTLA4. The present inventors have discovered that targeting the CD200 checkpoint overpowers the suppressive properties of CD200, PD-1 and CTLA4 checkpoints. The CD200 inhibitor is an effective and safe checkpoint inhibitor for immunotherapy against solid tumors.

The present invention in certain embodiments provides a method of inhibiting PD-1 in a cell by administering a CD200 activation receptor ligand (CD200AR-L) to the cell. In certain embodiments, the CD200AR-L is peptidomimetic. In certain embodiments, the peptidomimetic comprises one or more D-isomer amino acids. In certain embodiments, the peptidomimetic comprises one or more unnatural amino acids.

In certain embodiments, the CD200AR-L is a canine-specific peptide (cCD200AR-L).

In certain embodiments, the cell is a cancer cell.

In certain embodiments, the cancer cell is a glioblastoma cell.

In certain embodiments, the CD200AR-L is peptide P1A8, P2A0, P2A5, P3A12, or P4A10.

In certain embodiments, the CD200AR-L is peptide human P1A8.

In certain embodiments, the CD200AR-L is peptide human P2A0

In certain embodiments, the CD200AR-L is peptide human P4A10

In certain embodiments, the cell is a cancer cell.

In certain embodiments, the cancer cell is a glioblastoma cell.

The present invention in certain embodiments provides a method of enhancing efficacy of a tumor lysate vaccine in a mammal comprising administering a CD200 activation receptor ligand (CD200AR-L) to the mammal prior to the administration of the tumor lysate vaccine. In certain embodiments, the tumor lysate is substantially devoid of CD200. As used herein "substantially devoid" means that the substance (e.g., tumor lysate) has a diminished level of CD200, e.g., between 1-100% less CD200 than an unprocessed substance. In certain embodiments, the CD200 is removed by absorption using standard methods.

In certain embodiments, the CD200AR-L is a human-specific peptide (hCD200AR-L).

In certain embodiments, the CD200AR-L is a canine-specific peptide (cCD200AR-L).

In certain embodiments, the cell is a cancer cell.

In certain embodiments, the cancer cell is a glioblastoma cell.

In certain embodiments, the CD200AR-L is peptide P1A8, P2A0, P2A5, P3A12, or P4A10.

In certain embodiments, the CD200AR-L is peptide human P1A8.

In certain embodiments, the CD200AR-L is peptide human P2A0 In certain embodiments, the CD200AR-L is peptide human P4A10 In certain embodiments, the cell is a cancer cell.

In certain embodiments, the CD200AR-L is administered by local injection.

In certain embodiments, the tumor lysate vaccine is administered subcutaneously.

In certain embodiments, the tumor lysate vaccine is an autologous tumor lysate vaccine.

In certain embodiments, the mammal is administered the CD200AR-L from five to 14 days after surgically having tumor removed.

In certain embodiments, the mammal is administered the CD200AR-L about 10 days after surgically having tumor removed.

In certain embodiments, the (a) the species-specific CD200AR-L peptide is injected intradermally (ID), (b) twenty-four hours later, imiquimod is applied topically to the skin and allowed to absorb for 10-15 minutes, and (c) autologous tumor lysate mixed with CD200AR-L is injected intradermally.

In certain embodiments, the species-specific CD200AR-L peptide is injected intradermally (ID) at a dosage of about 5 μg/kg.

In certain embodiments, the imiquimod (1 packet) is applied topically to the skin at a dosage of 5% cream/12.5 g.

In certain embodiments, ~500 μg of protein of the autologous tumor lysate is mixed with about 5 μg/kg CD200AR-L and is injected intradermally.

In certain embodiments, the treatment regimen is repeated weekly for three weeks.

In certain embodiments, the treatment regimen is repeated weekly for three weeks, and then once every four weeks for three months, and then every 6-8 weeks as needed.

The term "mammal" as used herein refers to humans, higher non-human primates, rodents, domestic, cows, horses, pigs, sheep, dogs and cats. In one embodiment, the subject is a human. In one embodiment, the subject is a dog.

The present invention in certain embodiments provides a use of a pharmaceutical composition which that comprises a pharmaceutically acceptable carrier or diluent and, as an active ingredient, CD200AR-L, and optionally a cancer vaccine (e.g., a tumor lysate) as defined above for use or in the manufacture of a medicament for treating a disease or disorder arising from abnormal cell growth, function or behavior. In certain embodiments, the disease or disorder is cancer. In certain embodiments, the cancer is selected from solid tumors of the colon, breast, brain, liver, ovarian, gastric, lung, and head and neck. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention in certain embodiments provides a method of treating a disease or disorder arising from abnormal cell growth, function or behavior, which method comprises administering to a patient in need thereof a therapeutic regimen comprising a CD200AR-L and a cancer vaccine (e.g., a tumor lysate) administered sequentially. In certain embodiments, the therapeutic regimen is administered at least twice. In certain embodiments, the administration comprises administering at least three doses of the therapeutic regimen. In certain embodiments, the administration comprises administering at least five doses of the therapeutic regimen. In certain embodiments, the administration comprises administering at least ten doses of the therapeutic regimen. In certain embodiments, at least two consecutive dosages of the administration are separated by an interval of about one week, or about one month. In certain embodiments, the method further comprises administering an adjuvant before, concurrently or after administration of the therapeutic regimen.

In certain embodiments, the present invention comprises a method of reversing or modulating immune suppression in a patient having a disease or disorder arising from abnormal cell growth, function or behavior, which method comprises administering to a patient in need thereof the composition or therapeutic regimen described above.

In certain embodiments, the present invention comprises a method of reversing or modulating immune suppression in a tumor microenvironment or sentinel lymph nodes in a patient having a disease or disorder arising from abnormal cell growth, function or behavior, which method comprises administering to a patient in need thereof the composition or therapeutic regimen described above. In certain embodiments, the disease or disorder is cancer. In certain embodiments, the cancer is selected from glioblastoma, melanoma, prostate, endometrial, ovarian, breast, lung, head and neck, hepatocellular, and thyroid cancers.

In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

In certain embodiments, the present invention provides a method, wherein the delivering comprises administering the composition to the animal intravenously.

In certain embodiments, the present invention provides a method wherein the composition is administered to the animal using a systemic pump.

The term "therapeutically effective amount," in reference to treating a disease state/condition, refers to an amount of a therapeutic agent that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Cancer Vaccine

As described herein, a cancer vaccine may be a tumor antigen vaccine. Tumor antigen vaccines are vaccines made of cancer cells (e.g., tumor lysate), parts of cancer cells, or pure tumor antigens (substances isolated from tumor cells). A tumor antigen vaccine may stimulate the body's immune system to find and kill cancer cells. For example, the cancer vaccine may comprise glioma cancer cells, breast cancer cells, or other solid tumor cancer cells, or parts of these cells or antigens derived from these cells. In certain embodiments, the cancer vaccine comprises a vaccine antigen, wherein cultured tumor cell derived lysates are the source of the antigen.

Peptides and Peptidomimetic

In certain embodiments, the CD200AR-L is a peptide that has a length of 12 to 15 amino acids. For example, in certain embodiments, the peptide is 12, 13 14, or 15 amino acids in length.

In certain embodiments, the CD200AR-L is a human CD200AR-L:

P1:
(SEQ ID NO: 1)
IVTWQKKKAVSPENM

P2:
(SEQ ID NO: 2)
NITLEDEGCYMCLFN

P3:
(SEQ ID NO: 3)
VTFSENHGVVIQPAY

P4:
(SEQ ID NO: 4)
CLFNTFGFGKISGTA

In certain embodiments, the CD200AR-L is a canine CD200AR-L:

P4:
(SEQ ID NO: 5)
CLFNTFGSGKISGTA

In certain embodiments, the CD200AR-L is a murine CD200AR-L:

P1:
(SEQ ID NO: 17)
VTWQKKKAVSPENM

In certain embodiments, the CD200AR-L is a non-naturally occurring peptide that is not a product of nature. In certain embodiments, the CD200AR-L described herein comprises markedly different characteristics (e.g., structural, functional and/or other properties) as compared to naturally occurring peptides that correspond to a domain of CD200. The purity of the peptides was >95%, and each peptide was modified by N-terminal acetylation and C-terminal amidation to enhance its stability.

In certain embodiments, the CD200AR-L is peptide P1A8, P2A0, P2A5, P3A12, or P4A10. P1A8 (IVTWQK-KAAVSPENM) (SEQ ID NO: 6), P2A0 (NITLEDE-GCYMCLFN) (SEQ ID NO: 7), P2A5 (NITLADE-GCYMCLFN) (SEQ ID NO: 8), P3A12 (VTFSENHGVVIAPAY) (SEQ ID NO: 9), or P4A10 (CLFNTFGFGAISGTA) (SEQ ID NO: 10).

In certain embodiments, the CD200AR-L is a peptidomimetic. As used herein, a "peptidomimetic" is a small protein-like chain chemically designed to mimic a peptide. In certain, embodiments the peptidomimetic is designed to possess certain modulated molecular properties as compared to an unmodified peptide, such as enhanced stability (e.g., in vivo half-life) or biological activity. For example, a peptidomimetic may be generated by chemically modifying a peptide described herein. Chemical modifications include, but are not limited to, inclusion of D-isomer amino acids, β3 aza-amino acids, altered backbones and/or incorporation of unnatural amino acids. For example, these strategies are based on the replacement of natural (L-) amino acids with the unnatural (D-) amino acids or β3 aza-amino acids. Other strategies include the replacement of amide bonds (—CONH—) with thioamides or N-methylated amides. Other methods involve changing the N- and C-terminal amino acids to amides, esters, or D-amino acids.

Accordingly, in certain embodiments, the CD200AR-L is engineered to comprise one or more D-isomer amino acids.

In certain embodiments, the CD200AR-L comprises 1, 2, 3, 4, 5, 6, 7, 8, 9, 10, 11, 12, 13, 14, 15 or more D-isomer amino acids. In certain embodiments, about 10, 20, 30, 40, 50, 60, 70, 80, 90 or 100% of the amino acids are D-isomer amino acids.

In certain embodiments, the CD200AR-L is engineered to comprise one or more unnatural amino acids (e.g., dehydroalanine, homoserine, phosphoserine, phosphothreonine, phosphotyrosine, hydroxyproline, gamma carboxyglutamate; hippuric acid, octahydroindole 2-carboxylic acid, statine, 1,2,3,4, tetrahydroisoquinoline-3 carboxylic acid, penicillamine, ornithine, citruline, a methyl alanine, para benzoylphenylalanine, phenylglycine, propargylglycine, sarcosine, and tert butylglycine). In certain embodiments, a CD200 peptide inhibitor comprises 12, 13, 14, or 15 unnatural amino acids. In certain embodiments, about 10, 20, 30, 40, 50, 60, 70, 80, 90 or 100% of the amino acids are unnatural amino acids.

Use of CD200AR-L

As described herein, the CD200AR-L or a composition as described herein comprising a CD200AR-L may be used to reverse or modulate immune suppression. CD200 is an immunosuppressive protein that negatively regulates immune cells bearing the CD200R (e.g., suppresses antigen-specific CD8+ T cell responses). As described herein, "reversing or modulating immune suppression" refers to altering, impeding, reducing the immunosuppressive properties of the CD200 protein and/or tumor. In certain embodiments, the CD200 protein activity is reduced in a mammal by 1%, 2%, 3%, 4%, 5%, 10%, 20%, 30%, 40%, 50%, 60%, 70%, 80%, 90%, 100% as compared to the activity on the tumor in the absence of the CD200 protein. For example, immunosuppressive cells, such as myeloid-derived suppressor cells and regulatory T cells show increased activity while dendritic cells (DCs) appear to be impaired in tumors and sentinel lymph nodes in cancer patients. Accordingly, in certain embodiments, administration of CD200AR-L or a composition as described herein comprising a CD200AR-L could decrease the activity of immunosuppressive cells, such as myeloid-derived suppressor cells and regulatory T cells and/or could increase the activity of DCs in the tumor microenvironment and/or sentinel lymph nodes. In certain embodiments, reversal or modulation could be ascertained by assessing cytokine profiles as described herein (e.g., cytokine profiles could be determined before and after administration of a CD200AR-L and compared; see also, the Example).

As referred herein, the "tumor microenvironment" is the normal cells, molecules and blood vessels that surround and feed a tumor cell. A tumor can change its microenvironment and the microenvironment can affect how a tumor grows and spreads.

As described herein, CD200AR-L may enhance the efficacy of a cancer vaccine (e.g., when administered simultaneously or sequentially). For example, in certain embodiments the CD200AR-L and cancer vaccine may be in a combined formulation (i.e., a composition described herein) or may be in separate formulations for sequential or simultaneous administration.

As described herein, "enhancing efficacy" means a beneficial immune response is generated by the administration of a CD200AR-L and cancer vaccine that is greater than the beneficial immune response generated by the administration of just the cancer vaccine. In certain embodiments, administration of a CD200AR-L and a cancer vaccine (e.g., a composition described herein) reduces the size of a tumor (volume) in a mammal by 1%, 2%, 3%, 4%, 5%, 10%, 20%, 30%, 40%, 50%, 60%, 70%, 80%, 90%, 100% and this reduction is more than the reduction from administration the cancer vaccine alone. In certain embodiments, the administration of a CD200AR-L and a cancer vaccine (e.g., simultaneous or sequential administration) results in a synergistic effect.

Pharmaceutical Compositions

The present invention also provides, in certain embodiments, a pharmaceutical composition that comprises a pharmaceutically acceptable carrier or diluent and, as an active ingredient, a composition as described herein. In certain embodiments, the composition is formulated for oral administration or injection.

The present invention also provides, in certain embodiments, a composition as described herein for use in a method of treatment of a human or animal body by therapy.

The present invention also provides, in certain embodiments, a composition as described herein for use in medical therapy.

The present invention also provides, in certain embodiments, a composition as described herein for use in the treatment of a disease or disorder arising from abnormal cell growth, function or behavior.

The present invention also provides, in certain embodiments, the use of a composition as described herein in the manufacture of a medicament for treating a disease or disorder arising from abnormal cell growth, function or behavior. In certain embodiments, the disease or disorder is cancer. In certain embodiments, the cancer is selected from solid tumors of the colon, breast, brain, liver, ovarian, gastric, lung, and head and neck. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a method of treating a disease or disorder arising from abnormal cell growth, function or behavior, which method comprises administering to a patient in need thereof a composition as described herein. In certain embodiments, the disease or disorder is cancer. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a process for producing a pharmaceutical composition comprising combining a composition as described herein with a pharmaceutically acceptable carrier.

The present invention also provides, in certain embodiments, a kit for treating cancer, comprising: (a) a first pharmaceutical composition comprising a composition as described herein; and (b) instructions for use.

The present invention further provides nucleic acid sequences that encode the CD200AR-L peptides described above. The nucleic acids encoding the CD200AR-L peptides can be produced using the methods well known in the art (see, e.g., Sambrook and Russell, 2001).

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified composition can be isolated, lyophilized and stabilized. The composition may then be adjusted to an appropriate concentration, optionally combined with a suitable vaccine adjuvant, and packaged for use.

Adjuvants

An "adjuvant" is any molecule or compound that nonspecifically stimulates the humoral and/or cellular immune response. They are considered to be nonspecific because they only produce an immune response in the presence of an antigen. Adjuvants allow much smaller doses of antigen to be used and are essential to inducing a strong antibody response to soluble antigens. For example, when a therapeutic agent is administered in conjunction with an adjuvant, the therapeutic agent can be administered before, after, and/or simultaneously with the adjuvant. Adjuvants are known in the art and may include, but are not limited to, CpG oligonucleotides, Poly:ICLC and imiquimod.

Methods for Making Tumor Lysates

Tumor lysates are made by extracting a sample of the tumor to be treated from the subject. The tumor cells are then lysed. Methods of making effective tumor lysates include, but are not limited to, freeze thaw method, sonication, microwave, boiling, high heat, detergent or chemical-based cell lysis, electric or current-based lysis, and other physical methods, such as extreme force.

In certain embodiments, such as when a glioma is to be treated, EGF receptor VIII variant and IL-13 receptor alpha-2, which are glioma specific receptors (or expression vectors encoding these proteins), may be added to the tumor lysate.

Formulations and Methods of Administration

The vaccines and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Additional ingredients such as fragrances or antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations; such as multiple inhalations from an insufflator or by application of a plurality of drops into the eye.

In certain embodiments, the vaccine of the present invention reduces the size of the tumor in the subject by at least about 10%-100% (volume of tumor).

Definitions

"Bound" refers to binding or attachment that may be covalent, e.g., by chemically coupling, or non-covalent, e.g., ionic interactions, hydrophobic interactions, hydrogen bonds. Covalent bonds can be, for example, ester, ether, phosphoester, amide, peptide, imide, carbon-sulfur bonds, carbon-phosphorus bonds, and the like. The term "bound" is broader than and includes terms such as "conjugated," "coupled," "fused" and "attached."

The invention encompasses isolated or substantially purified protein (or peptide) compositions. In the context of the present invention, an "isolated" or "purified" polypeptide is a polypeptide that exists apart from its native environment and is therefore not a product of nature. A polypeptide may exist in a purified form or may exist in a non native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non protein of interest chemicals. Fragments and variants of the disclosed proteins or partial length proteins encoded thereby are also encompassed by the present invention. By "fragment" or "portion" is meant a full length or less than full length of the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., dehydroalanine, homoserine, phosphoserine, phosphothreonine, phosphotyrosine, hydroxyproline, gamma carboxyglutamate; hippuric acid, octahydroindole 2-carboxylic acid, statine, 1,2,3,4, tetrahydroisoquinoline-3 carboxylic acid, penicillamine, ornithine, citruline, a methyl alanine, para benzoylphenylalanine, phenylglycine, propargylglycine, sarcosine, and tert butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a (C1-C6)alkyl, phenyl or benzyl ester or amide; or as an α-methylbenzyl amide). Other suitable amino and carboxy protecting groups are known to those skilled in the art (See for example, T. W. Greene, Protecting Groups In Organic Synthesis; Wiley: New York, 1981, and references cited therein). The term also comprises natural and unnatural amino acids bearing a cyclopropyl side chain or an ethyl side chain.

The invention encompasses isolated or substantially purified protein compositions. In the context of the present invention, an "isolated" or "purified" polypeptide is a polypeptide that exists apart from its native environment. The terms "polypeptide" and "protein" are used interchangeably herein. An isolated protein molecule may exist in a purified form or may exist in a non native environment such as, for example, a transgenic host cell or bacteriophage. For example, an "isolated" or "purified" protein, or biologically active portion thereof, may be substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. In certain embodiments, an "isolated" or "purified" protein may include cell lysates. When the protein of the invention, or biologically active portion thereof, is recombinantly produced, preferably culture medium represents less than about 30%, 20%, 10%, or 5% (by dry weight) of chemical precursors or non protein of interest chemicals. Fragments and variants of the disclosed proteins or partial length proteins encoded thereby are also encompassed by the present invention. By "fragment" or "portion" is meant a full length or less than full length of the amino acid sequence of a protein.

By "variant" polypeptide is intended a polypeptide derived from the native protein by deletion (so called truncation) or addition of one or more amino acids to the N terminal and/or C terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred if little or no change in biological activity is desired.

Thus, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

"Operably linked" refers to the association of molecules so that the function of one is affected by the other.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, an antigen-presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g., using a 51Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

The invention will now be illustrated by the following non-limiting Examples.

EXAMPLE 1

CD200 Immune Checkpoint Reversal Combined with Autologous Tumor Vaccination for Glioblastoma Immunotherapy Recent advances in immunotherapy have included inhibition of immune checkpoint proteins in the tumor microenvironment and tumor-lysate-based vaccination strategies. Here we have combined these approaches in models of glioblastoma. Administration of a synthetic peptide targeting the immune checkpoint protein CD200 enhanced the capacity of antigen-presenting cells to induce a T-cell-mediated anti-glioblastoma effect. We found that in canine spontaneous gliomas, local injection of a canine-specific, CD200-directed peptide before subcutaneous delivery of an autologous tumor lysate vaccine prolonged survival relative to a historical control treated with autologous tumor lysate alone (median survivals of 12.7 months and 6.36 months, respectively). Antigen-presenting cells and T-lymphocytes primed with this peptide suppressed their expression of the inhibitory CD200 receptor, thereby enhancing their ability to initiate immune reactions in a glioblastoma microenvironment replete with the immunosuppressive CD200 protein. These results support the use of a CD200 ligand as a novel glioblastoma immunotherapeutic agent.

Immunotherapy is the third important wave in the history of cancer treatment. Clinical success of immune checkpoint blockade with monoclonal antibodies has led to an estimated 3000 immuno-oncology trials. The pertinence of immune checkpoints to tumor-vaccine-based therapeutic strategies, in contrast, has received less attention. In principle, the presence of immune checkpoint molecules in tumor vaccines would compromise the ability of the local antigen-presenting cells (APCs) to activate an adaptive immune response against tumor antigens, thereby compromising therapeutic efficacy.

During an adaptive immune response, expression of select cell-surface proteins downregulates or terminates immune activation. The observation that these proteins, known as immune checkpoint molecules, are expressed in solid tumors was a seminal discovery in immuno-oncology. These molecules interact with their cognate receptors on T-lymphocytes to suppress the signaling required for T-cell activation upon antigen presentation, thereby allowing the tumor to evade a subsequent immune response. These findings underlie efforts to develop immune checkpoint inhibitors to reverse immune suppression in the tumor microenvironment.

Here we examine whether an inhibitor of the CD200 (OX2) immune checkpoint augments the efficacy of an autologous tumor lysate vaccine against glioblastoma. Glioblastoma is the most common form of primary adult brain cancer. The prognosis of patients afflicted with glioblastoma remains dismal, with a median survival of 14.6 months after aggressive surgical resection, chemotherapy, and radiation therapy. Although the central nervous system (CNS) was once thought to be a site with immune privilege, subsequent studies have revealed that innate and adaptive immune responses play key roles in the host response to glioblastoma pathogenesis. This knowledge has led to the investigation of tumor vaccines as a therapeutic modality for glioblastomas. In this approach, antigens from a resected tumor are injected to elicit an immune response against any remaining tumor cells. However, glioblastomas express a number of immunosuppressive checkpoint molecules in the form of both cell-surface and soluble proteins that neutralize the host immune reactions to the tumor. In addition to immune suppression in the glioblastoma tumor microenvironment, these checkpoint molecules present formidable challenges for tumor-lysate-based vaccination strategies. The presence of one such checkpoint molecule in the lysate, CD200 (also known as OX2), compromises the ability of local APCs to initiate an adaptive immune response to tumor antigens.

CD200 is an immune checkpoint protein related to the B7 family of co-stimulatory receptors required for T-cell signaling. CD200-deficient mice exhibit auto-immune phenotypes, further substantiating CD200's role as an immune checkpoint protein. Importantly, CD200 is expressed in a wide spectrum of cancers, including chronic lymphocytic leukemia (CLL), multiple myeloma, acute myeloid leukemia, melanoma, ovarian tumors, metastatic small cell carcinoma, and glioblastoma. Although CD200 is expressed on tumor cell-surfaces, it is cleaved by metalloproteases such as ADAM 28 (A Disintegrin And Metalloprotease enzyme 28). Notably, the level of soluble CD200 in plasma correlates with tumor burden and survival in CLL patients. The physical interaction between cancer-released CD200 and its inhibitory receptor (CD200R1) on APCs (FIGS. 1A and 1B) suppresses secretion of pro-inflammatory cytokines, including interleukin 2 (IL2) and interferon γ (IFN γ); increases production of myeloid-derived suppressor cells (MDSCs) and regulatory T-cells (Tregs); and compromises the anti-tumor immune response.

Figure 1B:
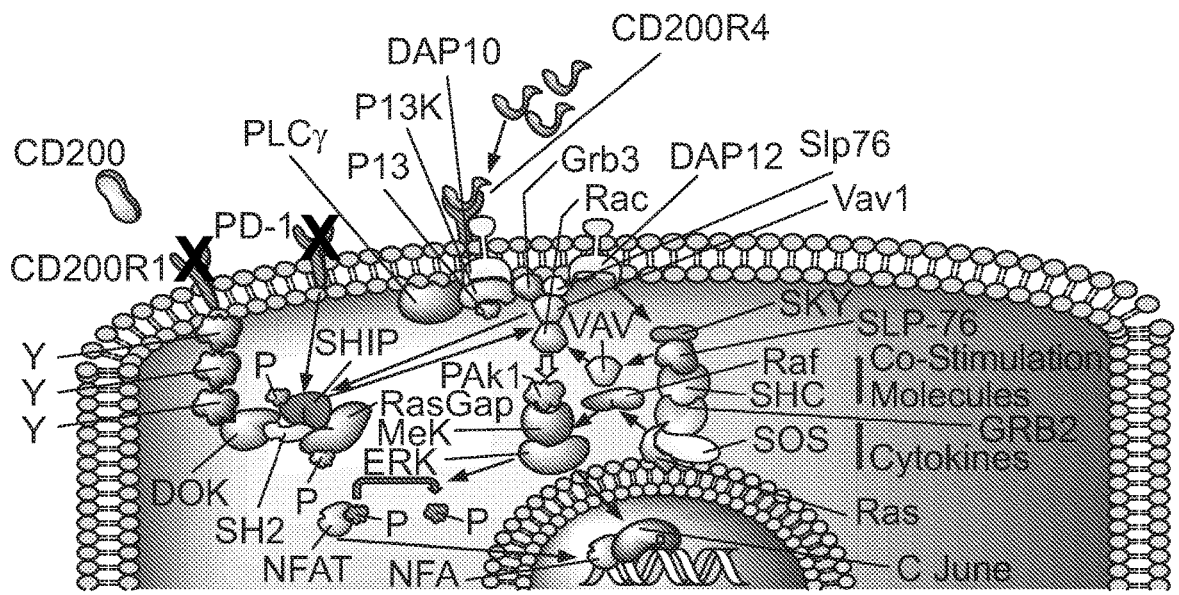

We previously demonstrated that the CD200-CD200R1 interaction is central to maintaining the glioblastoma immunosuppressive microenvironment and developed peptides targeting these interactions. Subsequent studies revealed that these peptides mediate their effects through a separate CD200 activation receptors (CD200AR), rather than through the inhibitory CD200R1 (FIGS. 1A and 1B). These findings suggest that peptides that mimic CD200 modulate CD200AR. Moreover, our previous murine experiments suggest that immuno-stimulation can be achieved by administering peptides that mimic CD200 as ligands (CD200AR-L) targeting CD200AR. We found the therapeutic effects of CD200 mimic peptides compelling and wished to translate these findings into the clinical setting. Because of sequence divergence between the human and murine CD200AR-L receptors, murine peptides were suboptimal for targeting human CD200AR. Here we describe the development of human and canine-specific CD200AR-Ls. We show that these peptides enhance the ability of human APCs to initiate anti-tumor responses. Importantly, local injection of the canine CD200AR-L prior to administration of a subcutaneous autologous tumor lysate vaccine significantly enhanced the efficacy of this vaccine in vivo in a canine spontaneous glioblastoma model.

Methods

Peptide synthesis. Peptides were designed based on 1) regions of the CD200 protein previously shown to interact with CD200AR and 2) sequences that show homology between murine, canine, and human CD200. Three 15-amino-acid peptides (P1, P3, and P4) and one 14-amino-acid peptide (P2) were synthesized (Thermo Fisher Scientific, Rockford, IL).

```
P1:
                                              (SEQ ID NO: 1)
IVTWQKKKAVSPENM

P2:
                                              (SEQ ID NO: 2)
NITLEDEGCYMCLFN

P3:
                                              (SEQ ID NO: 3)
VTFSENHGVVIQPAY

P4:
                                              (SEQ ID NO: 4)
CLFNTFGFGKISGTA
```

In certain embodiments, the CD200AR-L is a canine CD200AR-L:

```
P4:
                                              (SEQ ID NO: 5)
CLFNTFGSGKISGTA
```

In certain embodiments, the CD200AR-L is a murine CD200AR-L:

```
P1:
                                              (SEQ ID NO: 17)
VTWQKKKAVSPENM
```

The purity of the peptides was >95%, and each peptide was modified by N-terminal acetylation and C-terminal amidation to enhance its stability.

TCGA analysis. The Cancer Genome Atlas (TCGA) data portal (tcga-data.nci.nih.gov/tcga) was used to download survival times, death events, and RNAseq data for patients with glioblastoma. Cluster 3.0 (C Clustering Library 1.52) was used to $\log_2$ transform and mean-center the gene expression data and then to perform hierarchical average linkage clustering using the Pearson similarity metric on all genes with standard deviation>1.0. Gene clusters with a dendrogram node correlation>0.20 and at least 50 individual genes were identified, and associations with outcome were generated. Associations between the Gene Cluster Expression Summary Scores (GCESS) for the CD200R1-containing cluster and outcomes are reported based on Kaplan-Meier analyses of groups generated using quartiles of GCESS values. The list of genes co-localized to cluster 14 is included as CD200R1_cluster_gene list.xls.

Cytokine measurements. Human $CD14^+$ cells ($5 \times 10^5$) were isolated from peripheral blood mononuclear cells (PBMCs) using anti-CD14 beads (BD Biosciences, San Jose, CA), typically yielding ≥70% recovery and ≥90% purity. Cells were pulsed with 2 µM CD200AR-L peptide and incubated for 48 h, after which the supernatants were analyzed by bead array for cytokine production (BD Biosciences, San Jose, CA).

Dendritic cell differentiation. Cytomegalovirus (CMV)-positive HLA-A2$^+$ lymphocyte packs were obtained from the American Red Cross, and $CD14^+$ cells were purified. Approximately $1 \times 10^8$ $CD14^+$ cells were cultured in polystyrene tissue-culture flasks at 37° C. in 5% $CO_2$. GM-CSF (25 ng/mL) and IL-4 (40 ng/mL) were both added on days 3 and 5 to derive immature dendritic cells (iDCs).

CMV assay. iDCs ($5 \times 10^5$) were pulsed with 10 µg of CMV antigen peptide pp65495-503 (NLVPMVATV) and cultured as described above. The iDCs were then washed three times, and $5 \times 10^5$ $CD8^+$ T-cells from CMV-positive donors were co-incubated with the pulsed iDCs. CMV-negative PBMCs were used as a negative control. Supernatants were collected after 48 h of incubation and analyzed for IFNγ production by cytometric bead array (BD Biosciences).

Nanostring gene expression analysis: Total RNA from $CD14^+$ cells was sent to New Zealand Genomics Limited (Dunedin, New Zealand) to measure the expression of genes that are differentially expressed during inflammation (nCounter GX, NanoString Technologies, Seattle, WA, USA). Briefly, total RNA was extracted from $CD14^+$ cells (MagJET RNA kit, Thermo Fisher Scientific, Waltham, MA) using the protocol adapted for tissue (KingFisher Duo machine, Thermo Fisher Scientific, Waltham, MA). RNA samples were then quantified (Qubit® 2.0 fluorometer, Thermo Fisher Scientific) and subjected to RNA integrity analysis (2100 Bioanalyzer, Agilent Technologies, Santa Clara, CA). Probes for the genes encoding CD44 (NM_001001392.1); NANOG (NM_024865.2); OCT4 (NM_002701.4); STAT3 (NM_139276.2); and the housekeeping genes glucuronidase beta (NM_000181.1), clathrin heavy chain (NM 4859.2), and hypoxanthine phosphoribosyltransferase 1 (NM_000194.1) were designed and manufactured by NanoString Technologies.

Expression data obtained with NanoString GX were analyzed by using nSolver Analysis Software 3.0 (nanostring.com/products/nSolver) with default settings, and normalized to housekeeping genes. nSolver was used to perform cluster analysis and to generate heat maps by using Java Treeview Version 1.1.6r4. Pathway analysis was performed by using the PathCards Pathway Unification Database (pathcards.genecards.org). Student's t-tests were used to determine significant differences (p<0.05).

Canine study. Pet dogs with a solitary intra-axial mass found by magnetic resonance imaging (MRI) were recruited into a pilot study to assess the effect of a canine-specific peptide. The MRIs were performed to find the causes of generalized seizure activity or behavioral changes, and anti-epileptic drug therapy and corticosteroids were prescribed to control seizures and minimize cerebral edema, respectively. Additional inclusion criteria were 1) tumor suitable for surgical resection, 2) informed consent provided by the dog's owner, 3) normal mentation status at the time of surgery, and 4) no previous definitive therapy for the suspected glioma.

All dogs underwent surgical resection of the intra-axial mass for maximal tumor debulking. The removed tumors were immediately processed to generate autologous tumor lysates. The lysates were prepared by culturing single-cell suspensions from minced fresh tumor samples at 37° C. in 5% $O_2$. Cultured tumor cells were lysed by multiple freeze-thaw cycles and irradiated at 20 Gy. An immediate postoperative MRI was performed to assess the extent of resection and to quantify any residual tumor volume. Tumor volume was measured using the planimetry method, which outlines the tumor perimeter on each MR slice; Osirix software was used to calculate the area, and then the areas were summed and multiplied by slice thickness plus gap width. After recovery from anesthesia, all dogs were monitored in the intensive care unit for at least 24 hours. Anti-epileptic drugs (phenobarbital, levetiracetam, and zonisamide, alone or in combination) were continued after surgery, but the corticosteroid dose was tapered and discontinued within 10 to 14 days.

The first vaccination was given 10 days after surgery and was repeated weekly for 3 weeks, then once every 4 weeks for 3 months, and then every 6-8 weeks until tumor progression or death (FIG. 9). The vaccine protocol was as follows: the canine-specific CD200AR-L peptide (5 μg/kg) was injected intradermally (ID). Twenty-four hours later, imiquimod (1 packet 5% cream/12.5 g) was applied topically to the skin and allowed to absorb for 10-15 minutes prior to intradermal injection of autologous tumor lysate (~500 μg of protein) mixed with CD200AR-L (5 μg/kg). Disease status was monitored by MRI and physical examination at 4, 8, and 12 months after surgery, and then as needed if tumor recurrence was suspected.

Surgical resection was defined as gross total resection if there was no residual contrast-enhancement for gadolinium-enhancing lesions or T2-weighted FLAIR (fluid-attenuated inversion recovery) hyperintensity for non-enhancing lesions, near total resection if <10% of the original tumor volume remained, or subtotal resection if there was >10% residual tumor volume. Clinical response on follow-up MRIs was considered a complete response (CR) if there was no evidence of the tumor; partial response (PR) if the tumor volume had decreased by ≥65%; progressive disease (PD) if the tumor volume increased >40%; or stable disease if the response did not qualify as CR, PR, or PD as defined above. An MRI was performed if a dog developed recurrent or worsening neurologic signs before a scheduled MRI.

Results

Figure 2D:
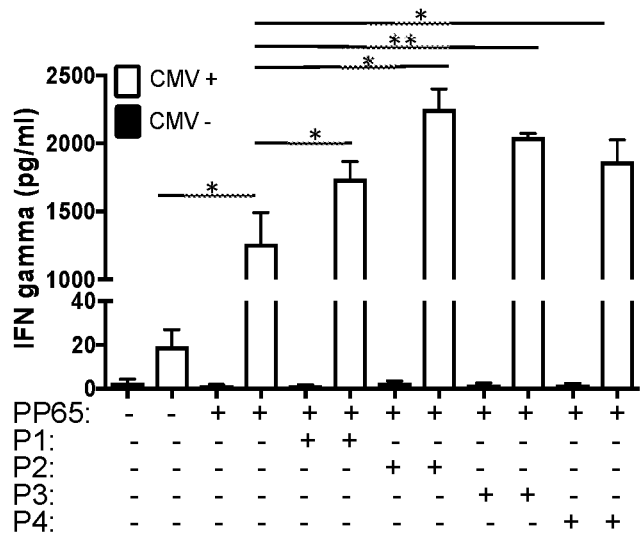

Design and identification of inhibitory peptides against CD200AR-L. Previous analyses of regions of CD200 that interact with CD200AR-L revealed four regions that share significant homology between humans, dogs, and mice (FIG. 2a). We generated four CD200AR-L peptides, termed P1-4, corresponding to these four regions in human CD200. To determine whether these peptides activate APCs, as previously observed for the murine CD200-mimic peptides, purified human $CD14^+$ cells were pulsed with the four different CD200AR-L peptides, and the supernatants were analyzed for immune-stimulatory cytokines (FIGS. 2b,c). We observed statistically significant increases in IL-1β p=0.0126, p=0.364, p=0.0022, p=0.0008) and TNFα (p=0.0146, p=0.0007, p=0.0022, and p=0.0082) in $CD14^+$ cells pulsed with P1, P2, P3, and P4, respectively, compared with non-pulsed controls. To determine whether these peptides generate an antigen-specific response, we used a CMV model in which T-cells from CMV-positive donors are primed with the CMV antigen pp65. Pulsing immature dendritic cells with CMV antigen pp65+CD200AR-L peptides elicited a significant antigen-specific response—the production of IFNγ—compared with pp65 alone (P1: p=0.034, P2: p=0.033, P3: p=0.0042, and P4: p=0.0202; FIG. 2d).

To create a peptide that maximally stimulates APCs, we substituted each amino acid of the four peptides with alanine, resulting in 61 alanine-substituted peptides. Purified $CD14^+$ cells were pulsed with these peptides, and response was measured as cytokine release. Five peptides were selected that maximally stimulated the secretion of inflammatory cytokines from $CD14^+$ cells: P1A8 (P1A8=P1 peptide with alanine substituted for the 8th amino acid), P2A0 (P1A0=P2 peptide with no alanine substitution), P2A5, P3A12, and P4A10.

Figure 3A:
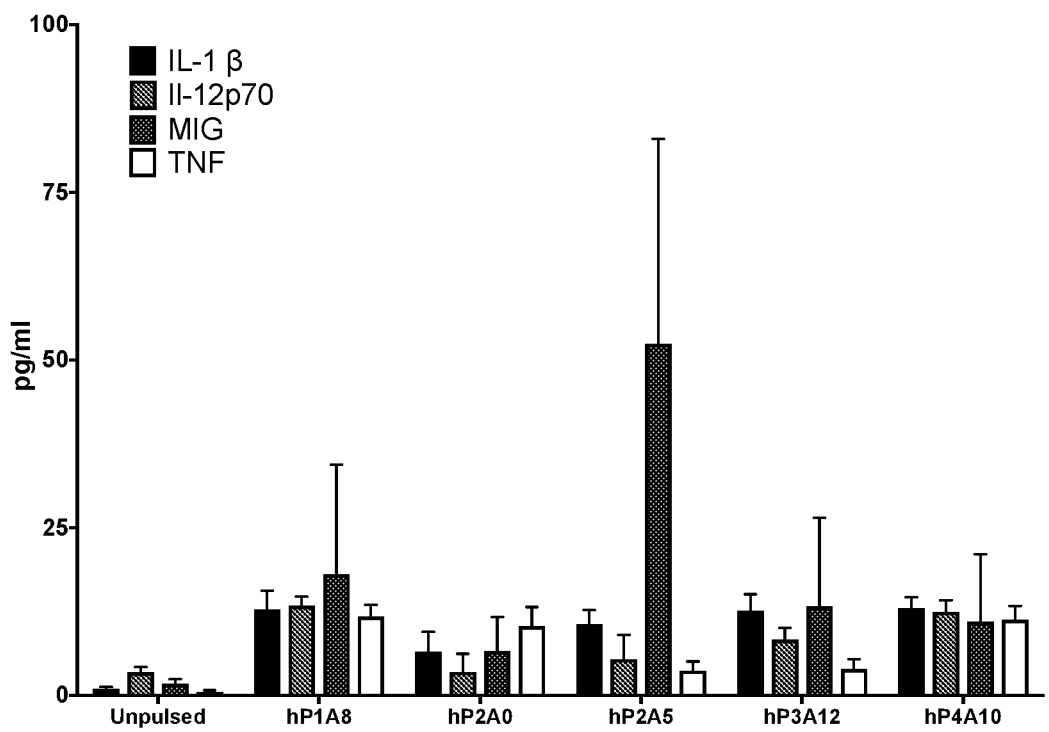
FIGS. 3A-3B. Alanine substitutions enhance antigen-presenting cell stimulation.
Figure 3B:
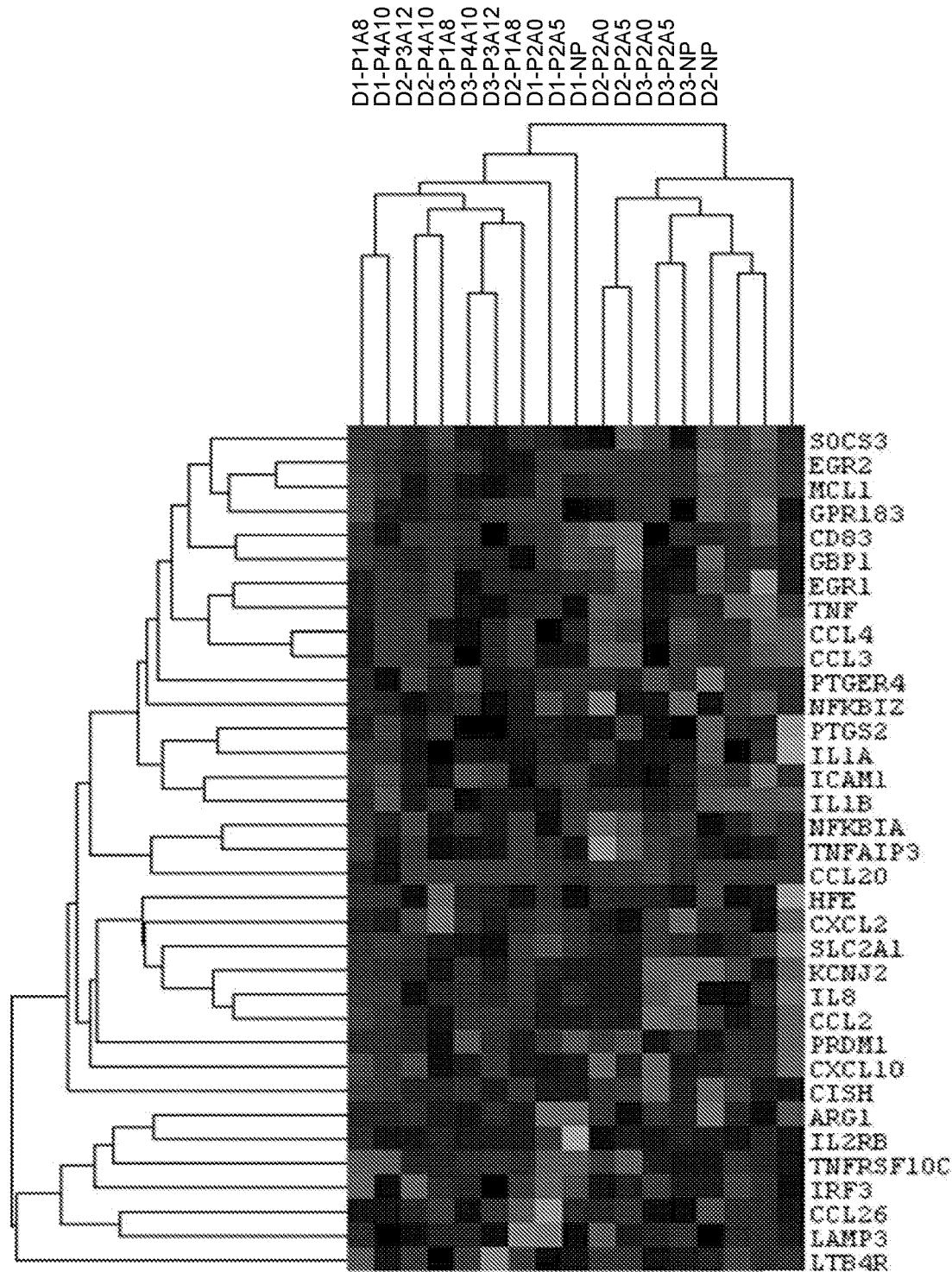

We next analyzed the effects of these peptides on a broader set of immune-stimulatory cytokines (including IL-12p70, MIG, and TNF) after they were used to pulse $CD14^+$ cells (FIG. 3a). Significant cytokine induction was observed after treatment with each of the five peptides. To characterize the effect of these peptides on $CD14^+$ cells, RNAseq was performed. Treatment with P1A8, P2A0, or P4A1 induced a notable increase in the mRNA expression of cytokines released in response to TNF signaling (Table 1, FIG. 3a), consistent with our previous result that CD200 exposure suppresses TNF signaling in APCs and CD200 mimics reverse this effectR. These results were recapitulated using a NanoString platform designed to detect the mRNA expression of TNF-regulated cytokines (FIG. 3b). The three peptides that most potently and consistently induced the mRNA expression of TNF-regulated cytokines (P1A8, P2A0, and P4A10) were selected for subsequent analysis.

TABLE 1

| Pathways | Gene Upregulation |
| --- | --- |
| LDL Oxidation in Atherogenesis | CCL2, CCL3, ICAM1, IL1B, TNF |
| Immune response, MIF-mediated glucocorticoid regulation | ICAM1, IL8, NFKBIA, PTGS2, TNF |
| EBV LMP1 signaling | CCL20, IL8, NFKBIA, TNF |
| Type II interferon signaling (IFNγ) | CXCL10, GBP1, ICAM1, IL1B, SOCS3 |
| Cytokines and Inflammatory Response | CXCL2, IL1A, IL1B, TNF |
| Canonical NF-kB pathway | NFKBIA, TNF, TNFAIP3 |
| IL-10 Pathway | IL1A, IL1B, SOCS3, TNF |
| IL-15 Signaling Pathways and their Primary Biological Effects in Different Immune Cell Types | CCL3, CCL4, TNF |
| Chemokine Superfamily Pathway: Human/Mouse Ligand-Receptor Interactions | CCL2, CCL20, CCL3, CCL4, CXCL10, CXCL2, IL8 |
| Chemokine Superfamily Pathway: Human/Mouse Ligand-Receptor Interactions | CCL2, ICAM1, IL1B, IL8, TNF |
| TNF signaling pathway | CCL2, CCL20, CXCL10, CXCL2, ICAM1, IL1B, NFKBIA, PTGS2, SOCS3, TNF, TNFAIP3 |

Targeting CD200 activation receptors enhances dendritic cell maturation. TNF-regulated cytokines (Table 1) have been implicated in dendritic cell maturation. The RNAseq results (FIG. 3b) therefore suggest that P1A8, P2A0, and P4A10 contribute to dendritic cell maturation. To substantiate this, $CD14^+$ cells were isolated from healthy human donors and pulsed with GM-CSF+IL4, P1A8, P2A0, or P4A10 27. Cells pulsed with P1A8, P2A0, and P4A10 expressed higher levels of the co-stimulatory molecules CD80, CD86, and HLA-DR than cells treated with GM-CSF+IL4 (p<0.0001; FIG. 4a). Moreover, we observed synergistic upregulation of CD80/86 and HLA-DR when CD14$^+$ cells were incubated with GM-CSF+IL4 and each of the peptides (p<0.0001) (FIG. 4b). These results suggest that P1A8, P2A0, and P4A10 enhanced the differentiation of CD14+ monocytes into iDC.

Figure 4C:
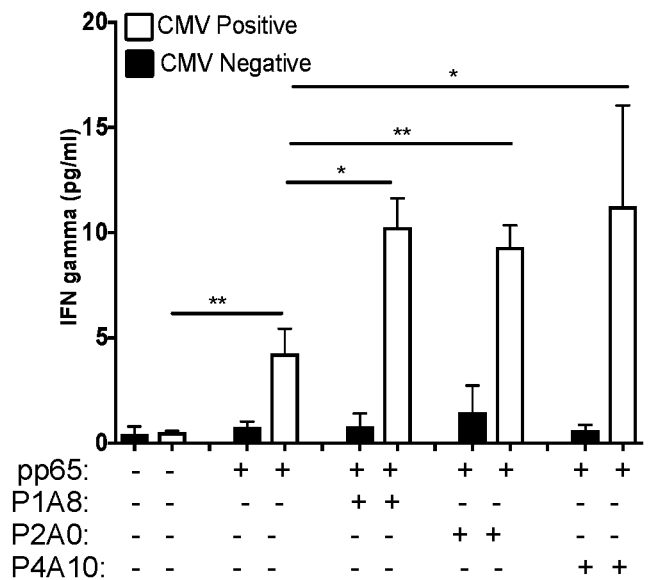
Figure 4D:
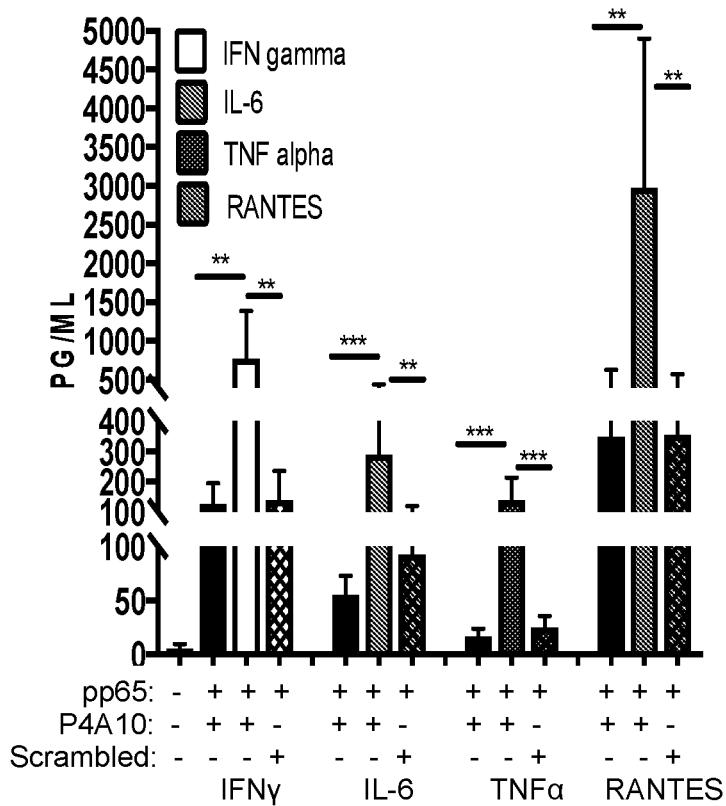

To assess the effects of P1A8, P2A0, and P4A10 on the antigen-specific response, we measured IFNγ release in the following assay. iDCs were pulsed with the CMV antigen pp65 with and without an equimolar amount of P1A8, P2A0, or P4A10. Autologous T-cells were then added and incubated with the iDCs for 48 h, after which IFNγ production was measured in the supernatants. Exposure to pp65 increased T-cell IFNγ production approximately 4-fold (FIG. 4c). Co-treatment of iDCs with pp65 and P1A8, P2A0, or P4A10 increased IFNγ release by an additional 2- to 3-fold over pp65 alone. These data show that P1A8, P2A0, or P4A10 enhanced the dendritic cells' ability to induce an antigen-specific response from human T-cells. Treatment of iDCs with P4A10, the most potent of the three peptides, enhanced T-cell secretion of IFNγ, IL6, TNFα, and RANTES by 5.4-, 5.6-, 16.6-, and 16.3-fold, respectively. A scrambled peptide control failed to enhance the pp65 response (FIG. 4d). These results suggest that P4A10 enhances the ability of APCs to induce a T-cell-mediated immune response.

Figure 5A:
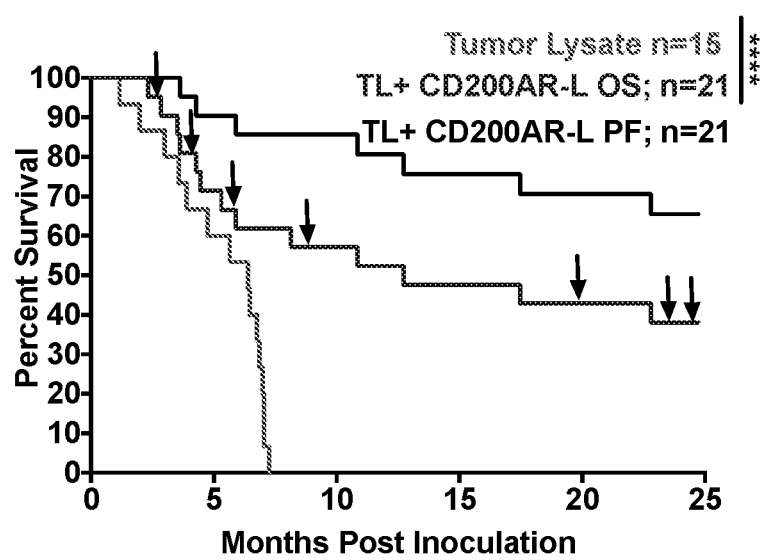
FIGS. 5A-5N. Treatment with the CD200 inhibitor induces tumor regression in dogs.

CD200AR-L peptide augments the efficacy of tumor lysate vaccination in a spontaneous canine glioma model. Our laboratory has a long-standing interest in the development of autologous tumor lysate vaccination as a strategy for treating glioblastomas. We postulate that the presence of immune checkpoint proteins in such lysates may compromise the efficacy of this therapy. Because the human P4A10 peptide has high homology with the canine peptide (FIG. 2a), we hypothesized that subcutaneous injection of the canine CD200AR-L before the introduction of autologous tumor lysate would enhance the efficacy of the vaccine in a canine model of spontaneously occurring glioblastoma. To test this hypothesis, 21 dogs with spontaneously occurring glioblastoma were treated with tumor resection and vaccinations consisting of canine CD200AR-L+autologous tumor lysate (FIG. 9). Tumor progression and overall survival were compared with historical data from a previous cohort of dogs treated with autologous tumor lysate alone after tumor resection. The extent of resection for these two cohorts was comparable. We observed a 25-month progression-free survival rate of 67% in dogs that received the canine CD200AR-L (FIG. 5a). Death was due to tumor recurrence in 33% (7/21) of the dogs, and 33% (7/21) of the dogs died or were euthanized for causes other than tumor progression. Two dogs without post-mortem examination were presumed to have died from tumor progression. In contrast, tumor progression was the cause of death in 100% (15/150) of the dogs in the group treated with tumor lysate alone. The median survival of dogs treated with canine CD200AR-L administration before autologous-tumor-lysate inoculation was 12.7 months. This survival compared favorably to the 6.36 month survival of dogs treated with tumor-lysate vaccination alone (FIG. 5a). One dog with tumor recurrence 18 months (548 days) after surgery was treated with a second surgery followed by autologous tumor lysate vaccine co-administered with the canine CD200AR-L, leading to an additional 9.93 months of survival, for a total of 28 months. This dog was not included in FIG. 5a.

Interestingly, six dogs had residual tumors of up to 50% following surgery, but tumor regression was seen on MRIs obtained 4 months after co-administration of CD200AR-L and tumor lysate vaccine (FIGS. 5b,c). Five dogs developed cerebral leukoencephalopathy characterized by T2 hyperintensity of the periventricular white matter tracts and ventricular dilatation. However, these signs resolved following corticosteroid treatment (FIGS. 5d&e). Vaccine therapy was also discontinued in one dog with severe clinical symptoms and, although the T2 hyperintensity resolved, tumor recurrence was noted on an MRI performed 2 months later (FIGS. 5f-5i). Vaccine and peptide therapy were reinitiated when the dog recovered and, at 2 months, tumor regression was seen again (FIGS. 5j-5m).

Figure 5N:
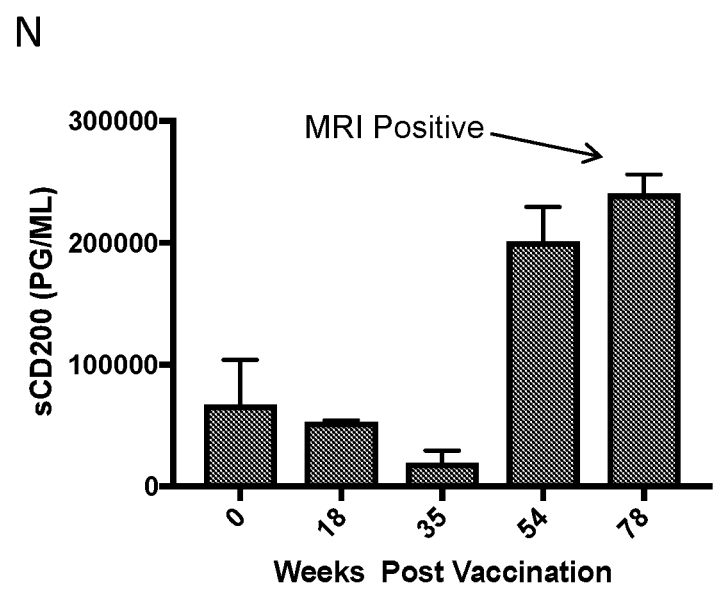

Because serum CD200 levels were previously shown to associate with tumor burden and overall survival in ependymoma patients, we collected and analyzed sera from the 21 canine subjects. Consistent with the previous study, we found a significant association between serum CD200 level and overall survival (FIG. 5n). Complete blood counts and serum chemistry profiles did not reveal obvious evidence of treatment-related adverse effects. These data suggest the potential utility of serum CD200 as a companion biomarker for P4A10-based therapeutic strategies.

Figure 6A:
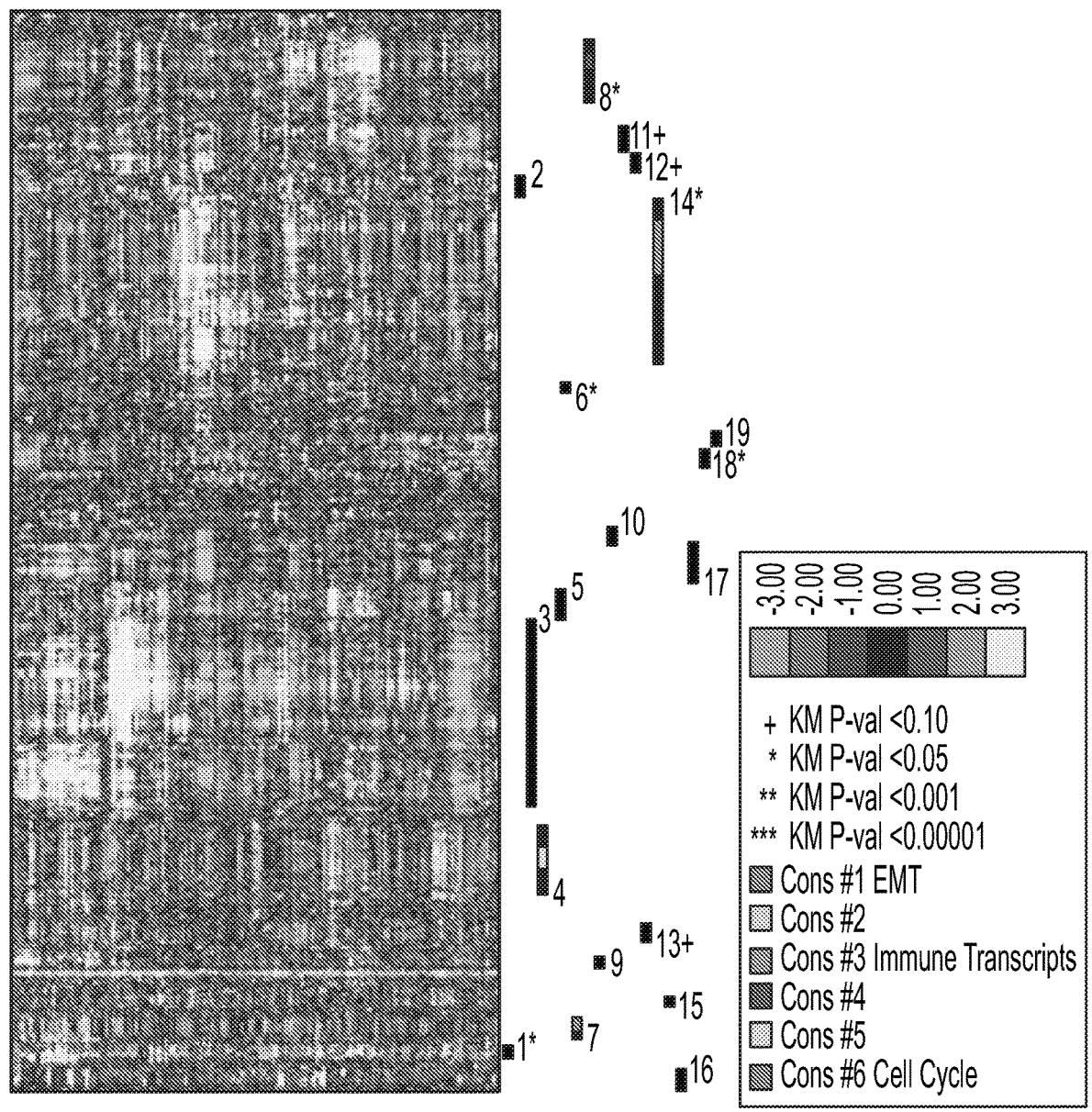
Figure 6D:
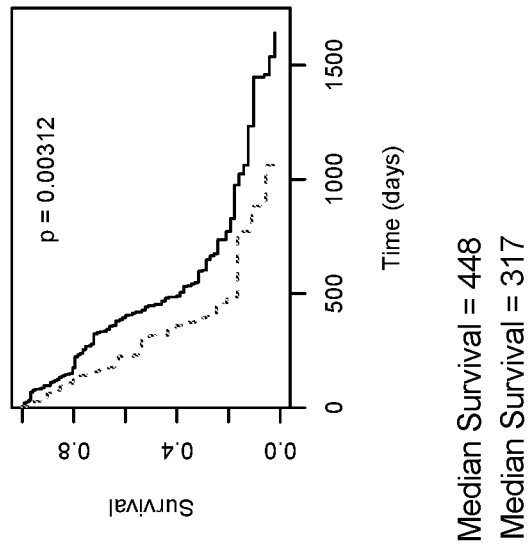
Figure 6C:
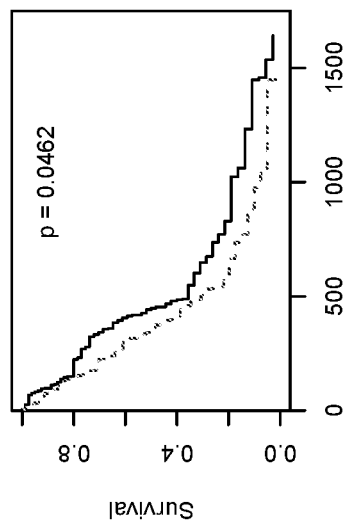
Figure 6B:
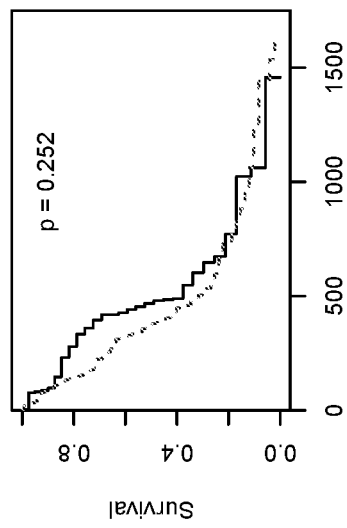

T-lymphocytes primed with P4A10 down-regulate expression of CD200R1. To examine whether CD200-related genes are associated with survival, we analyzed gene expression profiles of patient tumor samples in the TCGA dataset using GCESS24. This enabled us to identify clusters of genes that are concordantly expressed across the dataset and are associated with overall survival in an unbiased statistical analysis. CD200R1 expression was found within a large cluster of genes highly enriched in immune-related transcripts. Increased transcript levels of genes in this cluster were significantly associated with decreased survival (FIG. 6a, 6e). Patients who expressed high levels of the CD200R1-containing cluster (cluster 14) showed shorter overall survival times than patients who expressed lower levels of the cluster (FIGS. 6b-d). These results suggest the critical importance of the CD200/CD200R1 interaction in mediating an immunosuppressive glioblastoma microenvironment.

The efficacy of the P4A10+autologous tumor lysate strategy in this context creates an interesting conundrum. The T-cells that respond to APC presentation following stimulation express the inhibitory CD200R129. The immune-stimulatory effects of these primed T-cells, therefore, are expected to be blunted upon entry into a glioblastoma microenvironment that is replete with soluble and tumor-expressed CD200. However, we found that CD200AR-L priming prior to antigen presentation to T-cells suppressed the expression of the inhibitory CD200R1 on both APCs (p=0.0001) and T-cells (p=0.009) in our murine model (FIG. 7a,b), thereby rendering these cells resistant to the effect of CD200 in the glioblastoma tumor microenvironment. Supporting this hypothesis, we found that P4A10 priming prior to antigen presentation suppressed CD200R1 expression (FIG. 7d). Such suppression was not observed in mock-treated cells. Similar downregulation of PD-1 was observed on APCs (p=0.005, FIG. 7c). These results show that immune suppression in the CNS can be overcome through immuno-modulation occurring outside of the CNS.

Further, experiments were performed where human CD14 cells were pulsed with human CD200AR-L (P1A8), no pulsed cells were used as a control. Cells were isolated and analyzed for by flow cytometry (FIG. 7e) for levels of PD-1. The mean fluorescent intensity was analyzed for CD200R1 (FIG. 7f) and PD-1 expression (FIG. 7g). These experiments showed that the CD200AR-L down regulated the suppressive PD-1 receptor (FIG. 7g).

Discussion

Most immune checkpoint inhibitors are developed with the goal of reversing immune suppression in the tumor microenvironment. Here, we explored an alternate paradigm exploring the efficacy of immune checkpoint reversal at the site of autologous tumor vaccine inoculation. Our previous studies provided compelling data that the presence of the CD200 immune checkpoint protein in the tumor lysate suppressed the capacity of local APCs to activate the recruited T-cells and to trigger an effective anti-tumor immune response. We have built on this observation and tested whether a peptide that targets CD200-mediated immunosuppression, P4A10, can reverse the immune-suppressive effect of CD200. Our results indicated that P4A10 enhanced the ability of APCs to induce an antigen-specific response from human T-cells. Of note, CD200AR-L priming prior to antigen presentation to the T-cells suppressed the expression of inhibitory CD200R1, thereby rendering these cells resistant to the effect of CD200 in the glioblastoma tumor microenvironment. The intradermal injection of these immune-stimulatory molecules minimizes the likelihood of the systemic toxicities associated with systemic administration of immune modulators.

Although murine brain tumor models have yielded valuable insights into the etiology of glioblastomas, therapies that showed enormous promise in these models have frequently failed in clinical translation. Multiple expert panels have been assembled by the United States National Institutes of Health to address these failures, without any consensus for the optimal therapeutic model. In the absence of such consensus, therapeutic testing in animals other than mice warrants consideration before designing clinical trials. Our canine studies are particularly relevant in this context. Glioblastomas frequently arise spontaneously in certain breeds of dogs, including boxers, French bulldogs, and English bulldogs. This spontaneous canine "model" is an attractive platform for characterizing the immunologic effects of CD200 because 1) the tumors exhibit histologic features highly similar to those observed in human glioblastoma; 2) the tumors arise and grow in an immune microenvironment free from experimental manipulation; 3) there are substantial similarities in terms of immune cell populations in histopathologic samples of human and canine glioma; 4) as in their human counterparts, glioblastomas in dogs are typically detected at a late stage, when the tumor burden results in neurologic deficit; and 5) significant homology exists between human and canine CD200. When taken in this context, the efficacy of canine CD200AR-L in the canine model provides strong support for future human clinical trials.

In current clinical practice, evaluation of therapeutic response is largely based on the assessment of glioblastoma appearance on MRI. This practice is problematic because MRI is costly and the resolution of MR images is insufficient to detect tumor growth at the cellular level. There is therefore a critical need for minimally invasive biomarkers to assess glioblastoma growth. In many aspects, the biologic properties of CD200 render it well suited as a biomarker for tumor burden. Although CD200 is a cell-surface glycoprotein, most of the CD200 expressed in glioblastoma is released as a soluble factor 10. Independent groups, including data shown in this manuscript, have determined that the level of soluble CD200 in the sera of cancer patients correlates with tumor burden, which was supported by data shown in this manuscript (FIG. 5n). In aggregate, these results support serum CD200 as a potential "liquid biopsy" platform for glioblastoma monitoring.

In summary, our study provides data in support of the therapeutic efficacy of subcutaneous administration of an immuno-stimulatory peptide directed to interfering with the biologic function of the CD200 immune checkpoint prior to tumor vaccine administration as a novel therapy for glioblastoma.

EXAMPLE 2

CD200AR-L Overpowers PD-L1 Inhibitory Signals

Figure 8A:
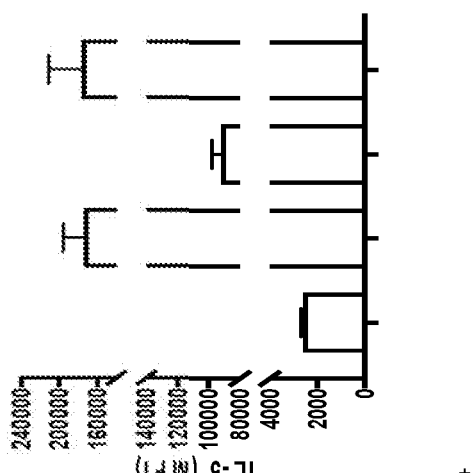
FIGS. 8A-8C. CD200AR-L pulses overpowers the suppressive PD-L1. Murine CD11b cells were activated with PMA and treated with PD-L1 or PD-L1+murine CD200AR-L. Following 48 hr, supernatants were harvested and analyzed for TNFalpha (FIG. 8A), IL4 (FIG. 8B), or IL5 (FIG. 8C). These experiments demonstrated that pulsing cells with the CD200AR-L overpowers the suppressive properties of PD-L1.
Figure 8B:
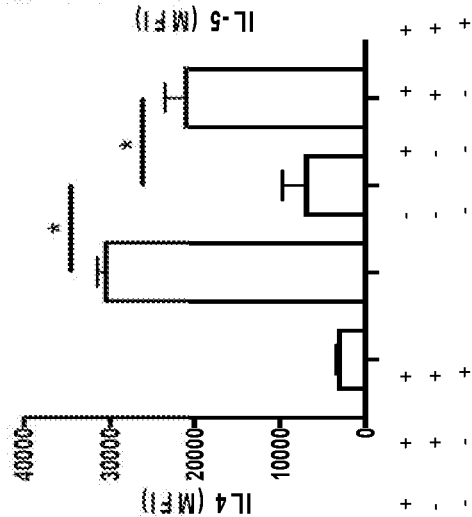
Figure 8C:
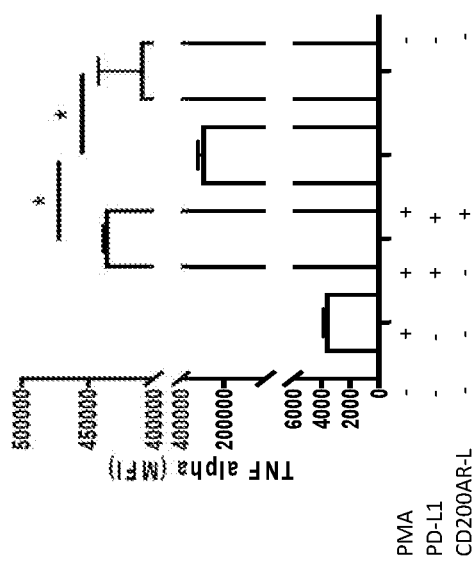

In these experiments, murine CD11b cells were stimulated with PMA and pulsed with PD-L1 with or without the murine CD200AR-L. These experiments showed that PD-L1 suppressed the activation of the CD11b cells, but the CD200AR-L overpowered the inhibitory effects of PD-L1 (FIGS. 8A-8C).

EXAMPLE 3

Effect of Suppressive Molecules (CD200 and PD-L1) on T Cell Inhibition

We propose that soluble CD200 and PD-L1 inhibit T cell activation through multiple checkpoints (FIG. 10). Therefore, the effect of multiple suppressive molecules (CD200 and PD-L1) on T cell inhibition was investigated. To accomplish this, total splenocytes were pulsed with CD200 or PD-L1, revealing an upregulation of CTLA4 on CD4 cells following CD200 treatment. In addition, following PD-L1 treatment, an upregulation of PD-L1 on CD11b and an upregulation of CTLA4 was observed on T cells. Being CTLA4 and PD-L1 propagate separate inhibitory signals, it was hypothesized that PD-L1 inhibits T cell activation through 1) direct CD200 and PD-L1 on T cells and 2) direct PD-L1 (on APCs)/PD-I (on APCs) producing cytokines upregulating CTLA4, which would explain the enhanced responses seen in combination α-PD-1 and α-CTLA4 treatments. However, neither of them inhibit CD200 effect on T cells.

The CD200 and PD-1 pathways crosstalk, allowing CD200AR-L to override the suppressive PD-L1. We established that treating animals with murine P1A12 (VTWQKK-KAVSPANM, SEQ ID NO: 15) and canine P4A10 CD200AR-L (CLFNTFGSGAISGTA, SEQ ID NO: 16) resulted in a significant survival benefit in both murine and canine glioma models. These results led us to hypothesize that CD200 and PD-1 might share common signaling pathways. To evaluate the effect of CD200AR-L on PD-1/PD-L1, splenocytes were activated with PMA+/−PD-L1 or PD-L1+CD200AR-L, and supernatants were analyzed for TNFα, IL-4 and IL-5 production (FIG. 11A-11C). As observed with the CD200 protein (FIG. 11B), PD-L1 induced an immune suppressed environment as measured by cytokine production; however, PD-L1 reduced the production of TNFα, IL-4 and IL-5 induced by PMA, which was restored by the addition of CD200AR-L. These experiments led to the hypothesis that the CD200 and PD-1 pathways are connected.

Figures 12A, 12B:
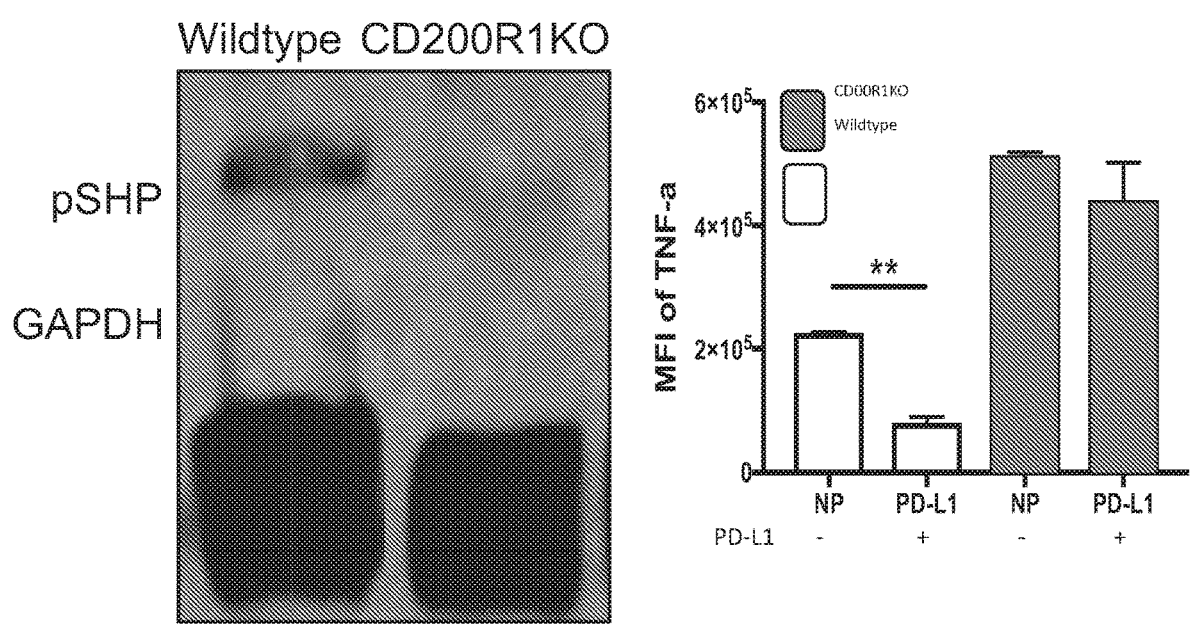
FIGS. 12A-12B. Effect of PD-L1 is inhibited by knocking out CD200R1.

CD200AR-L downregulates the expression of CD200R1 and PD-1. To further investigate the mechanism by which CD200AR-L prevents PD-L1 inhibition, CD11b cells were pulsed with CD200AR-L and the transcription levels of CD200R1 and PD-1 were analyzed (FIGS. 12A-12B). Both inhibitory receptors were downregulated by CD200AR-L. In addition, pulsing human CD14 cells with human CD200AR-L resulted in the same inhibition (FIGS. 12C-12D). CD11b cells from wildtype mice were pulsed with ovalbumin (OVA), which contains a well characterized protein SIINFEKL (SEQ ID NO: 14) to elucidate an antigen specific response. OVA+/−CD200AR-L, washed and CD3 cells were added to CD11b cells. These experiments demonstrated that CD200AR-L is capable of controlling the expression of CD200R1 and PD-1 on antigen presenting (CD11b and human CD14) and T cells, demonstrating the different checkpoints are interconnected.

CD200AR-L downregulates the expression of CD200R1 and PD-1. To further investigate the mechanism by which CD200AR-L prevents PD-L1 inhibition, CD11b cells were pulsed with CD200AR-L and the transcription levels of CD200R1 and PD-1 were analyzed (FIGS. 13A-13B). Both inhibitory receptors were downregulated by CD200AR-L. In addition, pulsing human CD14 cells with human CD200AR-L resulted in the same inhibition (FIGS. 13C-13D). CD11b cells from wildtype mice were pulsed with ovalbumin (OVA), which contains a well characterized protein SIINFEKL (SEQ ID NO: 14) to elucidate an antigen specific response. OVA+/−CD200AR-L, washed and CD3 cells were added to CD11b cells. These experiments demonstrated that CD200AR-L is capable of controlling the expression of CD200R1 and PD-1 on antigen presenting (CD11b and human CD14) and T cells, demonstrating the different checkpoints are interconnected.

CD200AR-L inhibits CTLA-4 upregulation. We next looked at the effects of CD200AR-L on T cell inhibition. In these experiments, splenocytes were pulsed with CD200 or PD-L1, revealing an upregulation of CTLA4 on CD4 cells, not on CD8 cells (FIG. 14A). In contrast to CD200, PD-L1 upregulated CTLA4 on both CD4 and CD8 T cells (FIG. 14A). Moreover, PD-L1, not CD200, upregulated the expression of PD-L1 on CD11b cells (FIG. 14C), potentially through soluble PD-L1/PD-1 (on CD11b) interactions. Being CTLA4 and PD-L1 propagate separate inhibitory signals, we hypothesize that PD-L1 inhibits T cell activation through two separate mechanisms, 1) through direct PD-L1 (on APCs)/PD-I (on T cells) interactions and through cytokine production following PD-L1 binding to the PD-1 on CD11b cell, which would explain the enhanced responses seen in combination α-PD-1 and α-CTLA4 treatments.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inhibiting PD-1 in a cell comprising or consisting of administering a CD200 activation receptor ligand (CD200AR-L) to the cell, wherein the CD200AR-L is peptide is 15 amino acids in length and consists of P1A8 (IVTWQKKAAVSPENM) (SEQ ID NO: 6), P2A5 (NITLADEGCYMCLFN) (SEQ ID NO: 8), P3A12 (VTFSENHGVVIAPAY) (SEQ ID NO: 9), or P4A10 (CLFNTFGFGAISGTA) (SEQ ID NO: 10).

2. The method of claim 1, wherein the cell is a cancer cell.

3. The method of claim 2, wherein the cancer cell is a glioblastoma cell.

4. A method of enhancing efficacy of a tumor lysate vaccine in a mammal comprising or consisting of administering a CD200 activation receptor ligand (CD200AR-L) to the mammal prior to the administration of the tumor lysate vaccine, wherein the CD200AR-L is peptide is 15 amino acids in length and consists of P1A8 (IVTWQKKAAVSPENM) (SEQ ID NO: 6), P2A5 (NITLADEGCYMCLFN) (SEQ ID NO: 8), P3A12 (VTFSENHGVVIAPAY) (SEQ ID NO: 9), or P4A10 (CLFNTFGFGAISGTA) (SEQ ID NO: 10).

5. The method of claim 4, wherein the cell is a cancer cell.

6. The method of claim 5, wherein the cancer cell is a glioblastoma cell.

7. The method of claim 4, wherein the CD200AR-L is administered by local injection.

8. The method of claim 4, wherein the tumor lysate vaccine is administered subcutaneously.

9. The method of claim 4, wherein the tumor lysate vaccine is an autologous tumor lysate vaccine.

10. The method of claim 4, wherein the mammal is administered the CD200AR-L from five to 14 days after surgically having tumor removed.

11. The method of claim 4, wherein the mammal is administered the CD200AR-L about 10 days after surgically having tumor removed.

12. The method of claim 4, wherein (a) the CD200AR-L peptide is injected intradermally (ID), (b) twenty-four hours later, imiquimod is applied topically to the skin and allowed to absorb for 10-15 minutes, and (c) autologous tumor lysate mixed with CD200AR-L is injected intradermally.

13. The method of claim 12, wherein the CD200AR-L peptide is injected intradermally (ID) at a dosage of about 5 µg/kg.

14. The method of claim 12, wherein the imiquimod (1 packet) is applied topically to the skin at a dosage of 5% cream/12.5g.

15. The method of claim 12, wherein ~500 µg of protein of the autologous tumor lysate mixed with about 5 µg/kg CD200AR-L and is injected intradermally.

16. The method of claim 12, wherein the treatment regimen is repeated weekly for three weeks.

* * * * *